United States Patent
St. John et al.

(10) Patent No.: US 7,910,135 B2
(45) Date of Patent: Mar. 22, 2011

(54) HYDROGEL WOUND DRESSING AND BIOMATERIALS FORMED IN SITU AND THEIR USES

(75) Inventors: John St. John, Grapevine, TX (US); Daniel G. Moro, Carrollton, TX (US)

(73) Assignee: ULURU Inc., Addison, TX (US)

(*) Notice: Subject to any disclaimer, the term of this patent is extended or adjusted under 35 U.S.C. 154(b) by 835 days.

(21) Appl. No.: 11/581,049

(22) Filed: Oct. 13, 2006

(65) Prior Publication Data
US 2009/0196936 A1    Aug. 6, 2009

(51) Int. Cl.
| | |
|---|---|
| A61K 9/14 | (2006.01) |
| A61K 35/00 | (2006.01) |
| A61F 2/00 | (2006.01) |
| A61K 38/00 | (2006.01) |
| A61K 31/715 | (2006.01) |
| A61K 31/65 | (2006.01) |
| A61K 31/167 | (2006.01) |
| A61K 31/7048 | (2006.01) |
| A61K 31/497 | (2006.01) |
| A61F 13/00 | (2006.01) |
| A01N 37/18 | (2006.01) |
| A01N 37/22 | (2006.01) |
| A01N 43/16 | (2006.01) |

(52) U.S. Cl. ............... 424/501; 424/93.1; 424/93.72; 424/422; 424/443; 424/487; 514/2; 514/12; 514/29; 514/54; 514/154; 514/254.11; 514/626; 977/906

(58) Field of Classification Search .................. None
See application file for complete search history.

(56) References Cited

U.S. PATENT DOCUMENTS

| | | | |
|---|---|---|---|
| 3,822,089 | A | 7/1974 | Wichterle |
| 3,948,841 | A | 4/1976 | Dusek |
| 3,951,925 | A | 4/1976 | Mishima et al. |
| 3,963,685 | A | 6/1976 | Abrahams |
| 4,272,518 | A | 6/1981 | Moro et al. |
| 4,542,176 | A | 9/1985 | Graham |
| 4,962,133 | A | 10/1990 | Chromecek et al. |
| 5,045,266 | A | 9/1991 | Moro et al. |
| 5,122,544 | A | 6/1992 | Bailey et al. |
| 5,266,325 | A | 11/1993 | Kuzma et al. |
| 5,292,515 | A | 3/1994 | Moro et al. |
| 5,468,811 | A | 11/1995 | Moro et al. |
| 5,536,508 | A * | 7/1996 | Canal et al. .................. 424/501 |
| 5,632,774 | A | 5/1997 | Babian |
| 5,770,631 | A | 6/1998 | Fukutomi et al. |
| 5,840,338 | A | 11/1998 | Roos et al. |
| 5,871,722 | A | 2/1999 | Nacht et al. |
| 5,945,457 | A | 8/1999 | Plate et al. |
| 6,068,859 | A | 5/2000 | Curatolo et al. |
| 6,306,177 | B1 | 10/2001 | Felt et al. |
| 6,521,431 | B1 | 2/2003 | Kiser et al. |
| 6,933,356 | B2 | 8/2005 | Hamamoto et al. |
| 7,351,430 | B2 | 4/2008 | St. John et al. |
| 2003/0093157 | A1 | 5/2003 | Casares et al. |
| 2003/0138490 | A1* | 7/2003 | Hu et al. .................. 424/486 |
| 2004/0086548 | A1 | 5/2004 | St. John et al. |
| 2005/0118270 | A1 | 6/2005 | Moro et al. |
| 2008/0063716 | A1 | 3/2008 | Moro et al. |

FOREIGN PATENT DOCUMENTS

| | | |
|---|---|---|
| CA | 2195373 | 7/1997 |
| EP | 0 785 224 B1 | 1/1997 |
| EP | 1447074 A2 * | 8/2004 |
| GB | 1 263 873 | 2/1972 |
| JP | 49-50089 | 5/1974 |
| JP | 53040038 A | 4/1978 |
| JP | 58-331 | 1/1983 |
| JP | 58149910 A | 9/1983 |
| JP | 05247225 A | 9/1993 |
| JP | 9-25303 | 1/1997 |
| JP | 9-208710 | 8/1997 |
| JP | 2001-517494 | 10/2001 |
| JP | 2002284882 A | 10/2002 |
| JP | 2002302616 A | 10/2002 |
| JP | 2003261777 A | 9/2003 |
| WO | WO 99/15211 A1 | 4/1999 |
| WO | WO 03/026537 A1 | 4/2003 |
| WO | WO 2006/041967 A1 | 4/2006 |

OTHER PUBLICATIONS

Tauer et al. (Colloid Polym Sci 2005, 283, 351-358).*
Zhou et al. (J. Phys. Chem B 1998, 102, 1364-1371).*
Attivi et al. (Drug Development and Industrial Pharmacy 2005, 31, 179-189).*
Jones et al. (Pharmaceutical Applications of Polymers for Drug Delivery. Sherwebury:Rapra Technology Ltd. 2004, eBook, p. 38).*
Lanza et al. (Nature Biotechnology 1996, 14, 1107-1111.*

(Continued)

*Primary Examiner* — Johann R Richter
*Assistant Examiner* — Jessica Kassa
(74) *Attorney, Agent, or Firm* — Antoinette F. Konski; Foley & Lardner LLP

(57) ABSTRACT

The present invention relates to a method of forming shape-retentive and shape-conforming aggregate wound dressings and biomaterials composed of gel nanoparticles and wound or bodily fluid in which the aggregates are held together by non-covalent bond physical forces such as, without limitation, hydrophobic-hydrophilic interactions and hydrogen bonds. The method comprises introducing a dry powder of gel nanoparticles to a wound site in which the nanoparticles absorb some of the blood or wound exudate and coalesce in situ into the claimed shape-retentive aggregate dressing. The method also comprises introducing the dry nanoparticle powder in or on a wet bodily tissue in vivo to form the claimed shape-retentive biomaterial. In addition, the method also comprises incorporating biomedical agents to produce medicated aggregate dressings or biomaterials for a variety of medical applications. This invention also relates to uses of the method of formation of the shape-retentive aggregates of gel nanoparticles.

48 Claims, 9 Drawing Sheets
(9 of 9 Drawing Sheet(s) Filed in Color)

OTHER PUBLICATIONS

Horak et al., "New radiopaque polyHEMA-based hydrogel particles," J. of Biomedical Materials Research, vol. 34, pp. 183-188, 1997.

Ruckenstein et al., "Polymerization in gel-like emulsions," J. of applied Polymer Science, vol. 36, pp. 907-923, 1988.

U.S. Appl. No. 10/289,756 (now U.S. Patent No. 7,351,430)—Notice of Allowance dated Nov. 8, 2007.

U.S. Appl. No. 10/289,756 (now U.S. Patent No. 7,351,430)—Non-Final Office Action dated Jun. 14, 2007.

U.S. Appl. No. 10/289,756 (now U.S. Patent No. 7,351,430)—Advisory Action dated Jan. 29, 2007.

U.S. Appl. No. 10/289,756 (now U.S. Patent No. 7,351,430)—Final Office Action dated Oct. 12, 2006.

U.S. Appl. No. 10/289,756 (now U.S. Patent No. 7,351,430)—Non-Final Office Action dated Apr. 19, 2006.

U.S. Appl. No. 10/289,756 (now U.S. Patent No. 7,351,430)—Final Office Action dated May 17, 2005.

U.S. Appl. No. 10/289,756 (now U.S. Patent No. 7,351,430)—Non-Final Office Action dated Apr. 6, 2004.

U.S. Appl. No. 10/960,461—Non-Final Office Action dated Mar. 18, 2009.

U.S. Appl. No. 10/960,461—Non-Final Office Action dated Jun. 23, 2008.

U.S. Appl. No. 10/960,461—Restriction Requirement dated May 2, 2008.

U.S. Appl. No. 11/929,531—Non-Final Office Action dated Mar. 19, 2009.

U.S. Appl. No. 11/929,531—Non-Final Office Action dated Jun. 25, 2008.

Klein et al. (2003), "Preparation of Monodisperse PMMA Microspheres in Nonpolar Solvents by Dispersion Polymerization with a Macromonomeric Stabilizer," *Colloid Polym. Sci.* 282:7-13.

*Radiation Synthesis and Modification of Polymers for Biomedical Applications: Final results of a coordinated research project* (Dec. 2002), International Atomic Energy Agency, Vienna, Austria.

Szkurhan & Georges (2004), "Stable Free-Radical Emulsion Polymerization," *Macromolecules* 37:4776-4782.

International Search Report for WO 2004/043438 A1.

U.S. Appl. No. 11/929,534, filed Oct. 30, 2007, John V. St. John, et al.

U.S. Appl. No. 11/686,902, filed Mar. 15, 2007, Shannon et al.

International Search Report for WO 2006/041967 A1.

Zeta-Meter, Inc., "Zeta-Potential: A Complete Course in 5 Minutes," Accessed from http://www.zeta-meter.com/5min.pdf via the Wayback Machine (Jun. 6, 2001).

Am Ende, et al., "Transport of ionizable drugs and proteins in crosslinked poly(acrylic acid) and poly(acrylic acid-co-2-hydroxyethyl methacrylate)," *Journal of Controlled Release* (1997), vol. 48, pp. 47-56.

Ayhan, F. et al., "Optimization of urease immobilization onto non-porous HEMA incorporated poly(EGDMA) microbeads and estimation of kinetic parameters," *Bioresource Technology* (2002) vol. 81, pp. 131-140.

Beers, K. L. et al., "Atom Transfer Radical Polymereization of 2-Hydroxyethyl Methacrylate," *Macromolecules* (1999), vol. 32, pp. 5772-5776.

Bouillaguet, S. et al., "Effect of sub-lethal concentrations of HEMA (2-hydroxyethyl methacrylate) on THP-1 human monocyte-macrophages, in vitro," *Dental Materials* (2000), vol. 16, pp. 213-217.

Brahim, S. et al., "Kinetics of glucose oxidase immobilized in p(HEMA)-hydrogel microspheres in a packed-bed bioreactor," *Journal of Molecular Catalysis B: Enzymatic* (2002), vol. 18, pp. 69-80.

Brier-Russell, D. et al., "In Vitro Assessment of Interaction of Blood with Model Surfaces: Acrylates and Methacrylates," *journal of Colloid and Interface Science* (1981), vol. 81, pp. 311-318.

Dalton, P. D. et al., "Manufacture of poly(2-hydroxyethyl methacrylate-co-methyl methacrylate) hydrogel tubes for use as nerve guidance channels," *Biomaterials* (2002), vol. 23, pp. 3843-3851.

Debord, J.D. et al., "Thermoresponsive Photonic Crystals," *The Journal of Physical Chemistry* (2000), vol. 104, No. 27, pp. 6327-6331.

Denizli, A. et al., "Monosize and non-porous p(HEMA-co-MMA) microparticles designed as dye- and metal-chelate affinity sorbents," *Colloids and Surfaces A: Physicochemical and Engineering Aspects* (2000), vol. 174, pp. 307-317.

Dziubla, T. D. et al., "Evaluation of porous networks of poly(2-hydroxyethyl methacrylate) as interfacial drug delivery devices," *Biomaterials* (2001), pp. 2893-2899.

Frutos, P. et al., "Release of gentamicin sulphate from a modified commercial bone cement. Effect of (2-hydroxyethyl methacrylate) comonomer and poly(N-vinyl-2-pyrrolidone) additive on release mechanism and kinetics," *Biomaterials* (2002), vol. 23, pp. 3787-3797.

Gallardo, A. et al., "Controlled release of cyclosporine from VP-MEMA copolymer systems of adjustable resorption monitorized by MEKC," *Biomaterials* (2000), vol. 21, pp. 915-921.

Gallardo, A. et al., "Modulated release of cyclosporine from soluble vinyl pyrrolidone-hydroxyethyl methacrylate copolymer hydrogels A correlation of 'In vitro' and 'In vivo' experiments," *Journal of Controlled Release* (2001), vol. 72, pp. 1-11.

Garrett, Q. et al., "Effect of charged groups on the adsorption and penetration of proteins onto and into carboxymethylated poly(HEMA) hydrogels," *Biomaterials* (1998), vol. 19, pp. 2175-2186.

Graham, N. B. et al., "Nanogels and microgels: The new polymeric materials playground," *Pure & Appl. Chem.* (1998), vol. 70, No. 6, pp. 1271-1275.

Hacioglu, B. et al., "Polymerization kinetics of HEMA/DEGMA: using changes in initiation and chain transfer rates to explore the effects of chain-length-dependent termination," *Biomaterials* (2002), vol. 23, pp. 4057-4064.

Horak, D. et al., "Hydrogels in endovascular embolization," *Biomaterials* (1997), vol. 18, pp. 1355-1359.

Hsiue, G. et al., "Poly(2-hydroxyethyl methacrylate) film as a drug delivery system for pilocarpine," *Biomaterials* (2001), vol. 22, pp. 1763-1769.

Hu, Z. et al., "Polymer Gel Nanoparticle Networks," *Advanced Materials* (2000), vol. 12, No. 16, pp. 1173-1176.

Huang et al. "Controlled drug release from hydrogel nanoparticle networks" *J. Control. Release* (2004) 94:303-311.

Hutcheon, G.A. et al., "Water absorption and surface properties of novel poly(ethylmethacrylate) polymer systems for use in bone and cartilage repair," *Biomaterials* (2001), vol. 22, pp. 667-676.

Klisch, J. et al., "Combined stent implantation and embolization with liquid 2-polyhydroxyethyl methacrylate for treatment of experimental canine wide-necked aneurysms," *Interventional Neuroradiology* (2002), vol. 44, pp. 503-512.

Lesny, P. et al., "Polymer hydrogels usable for nervous tissue repair," *Journal of Chemical Neuroanatomy* (2002), vol. 23, pp. 243-247.

Liu, Q. et al., "Preparation of macroporous poly(2-Hydroxyethyl methacrylate) hydrogels by enhanced phase separation," *Biomaterials* (2000), vol. 21, pp. 2163-2169.

Lyon, L. A. et al., "Responsive Microgel Photonic Crystals," *Polymer Preprints* (2002), vol. 43, pp. 24-25.

Lyon, L. A. et al., "Tunable Kinetics of Core-Shell Microgel Volume Phase Transitions," *Polymer Preprints* (2002), vol. 43, pp. 363-364.

Noda, M. et al., "Sublethal, 2-week exposures of dental material components alter TNF-$\alpha$ secretion of THP-1 monocytes," *Dental Materials* (2003), pp. 1-5.

Nojiri, C. et al., "Nonthrombogenic Polymer Vascular Prosthesis," *Artificial Organs* (1995), vol. 19, No. 1, pp. 32-38.

Pashley, D. H. et al., "Permeability of demineralized dentin to HEMA," *Dental Materials* (2000), vol. 16, pp. 7-14.

Ramakrishna, S. et al., "Biomedical applications of polymer-composite materials: a review," *Composites Science and Technology* (2001), vol. 61, pp. 1189-1224.

Reichl, F. X., "Biological clearance of HEMA in guinea pigs," *Biomaterials* (2002), vol. 23, pp. 2135-2141.

Robinson, K. L., "Controlled Polymerization of 2-Hydroxyethyl Methacrylate by ATRP at Ambient Temperature," *Macromolecules* (2001), vol. 34, pp. 3155-3158.

Rogach, A. L. et al., "Electrophoretic Deposition of Latex-Based 3D Colloidal Photonic Crystals: A Technique for Rapid Production of High-Quality Opals," *Chem Mater.* (2000), vol. 12, pp. 2721-2726.

Sefc, L. et al., "Development of hydrogel implants for urinary incontinence treatment," *Biomaterials* (2002), vol. 23, pp. 3711-3715.

Sefton, M. V. et al., "Making microencapsulation work: conformal coating, immobilization gels and in vivo performance," *Journal of Controlled Release* (2000), vol. 65, pp. 173-186.

Seidel, J. M. et al., "Synthesis of PolyHEMA Hydrogels for Using as Biomaterials," *Materials Research* (2000), vol. 3, No. 3, pp. 79-83.

Tanaka, M. et al., "Study on kinetics of early stage protein adsorption on poly(2-methoxyethylacrylate) (PMEA) surface," *Colloids and Surfaces A: Physicochemical and Engineering Aspectsl* (2002), vol. 203, pp. 195-204.

Tanaka, M. et al., "Blood compatible aspects of poly(2-methoxyethylacrylate) (PMEA)—relationship between protein adsorption and platelet adhesion on PMEA surface," *Biomaterials* (2000), vol. 21, pp. 1471-1481.

Yoshi, E., "Cytotoxic effects of acrylates and methacrylates: Relationships of monomer structures and cytotoxicity," *J. Biomed Mater. Res.* (1997), vol. 37, pp. 517-524.

U.S. Appl. No. 11/929,531—Final Office Action dated Oct. 14, 2009.

U.S. Appl. No. 10/960,461—Notice of Allowance dated Nov. 12, 2009.

Landfester et al. (2000) "Preparation of Polymer Particles in Nonaqueous Direct and Inverse Miniemulsions," *Macromolecules* 33:2370-2376.

Takahashi et al. (1996) "Preparation of Micro-Size Monodisperse Poly(2-hydroxyethyl methacrylate) Particles by Dispersion Polymerization," *Journal of Polymer Science: Part A: Polymer Chemistry* 34:175-182.

U.S. Appl. No. 11/686,902 - Non-Final Office Action dated Oct. 4, 2010.

U.S. Appl. No. 10/960,461 - Notice of Allowance dated Aug. 18, 2010.

International Search Report for WO 2004/043438 A1, 2004.

International Search Report for WO 2006/041967 A1, 2006.

Na & Bae (2002) "Self-Assembled Hydrogel Nanoparticles Responsive to Tumor Extracellular pH from Pullulan Derivative/Sulfonamide Conjugate: Characterization, Aggregation, and Adriamycin Release in Vitro" Pharmaceutical Research 19(5):681-688.

Thornton et al. (2004) "Shape Retaining Injectable Hydrogels for Minimally Invasive Bulking" The Journal of Urology 172:763-768.

\* cited by examiner

HYDROGEL WOUND DRESSING AND BIOMATERIALS FORMED IN SITU AND THEIR USES

FIELD OF THE INVENTION

This invention relates to the fields of organic chemistry, physical chemistry, polymer chemistry, pharmaceutical chemistry, medicine and material science.

BACKGROUND OF THE INVENTION

The principal function of a wound dressing is to provide an optimum healing environment. No one dressing is appropriate for all wounds and the choice of a wound dressing is dependent on the cause, presence of infection, wound type and size, stage of wound healing, cost, and patient acceptability (Findlay D., Aust. Fam Physician, 1994:23(5):824-839). According to Lawrence (Lawrence, J. C., Injury, 1982; 13:500-512), dressing material should be sterile, strong, absorbent, protective, inexpensive, and conform to the contours of the body. It should be nontoxic, hypoallergenic, and free of particulate material that may shed into the wound. Also, it should be easy to remove without it adhering to the wound and have an acceptable appearance to patients, nursing staff, and others.

Wound dressings can be classified as either primary or secondary. Primary dressings are placed directly over the wound. They provide protection, support, and absorption, prevent desiccation and infection, and serve as an adhesive base for the secondary dressing. Secondary dressings provide additional support, absorption, protection, compression, and occlusion. Often the secondary dressing serves as a pressure dressing.

There are a wide variety of dressings available to accomplish the essential goals of topical therapy, which are to provide adequate oxygen and circulation to the tissues, insulate and protect the healing wound, eliminate clinical infection by removing excess exudate, maintain a clean and moist environment, and obtain complete wound closure. Several different types of products may be needed as the wound progresses through the healing stages. These products include alginates, which form a gel covering over the wound, cleansers, which clean the wound site, collagen, a non-adherent covering that stimulates cellular migration, composites and enzymatic debriders, which facilitate autolytic debridement, exudate absorbers and foams, which fill the dead space in a wound, medicated gauze products, to treat and control infection, hydrocolloids and hydrogels, which reduce pain and facilitate autolytic debridement, pouches, to collect and contain drainage, skin sealants, and transparent films which reduce friction and facilitate autolytic debridement (Robert G. Smith, Wound Care Product Selection, U.S. Pharmacist, 4/2003). These products have attributes in treating various and different stages of wounds, however all have limitations. For example, alginates can possibly dehydrate the wound bed, give off foul odors and are contraindicated for use in the presence of dry eschar, on third degree burns and surgical implantation. Collagen dressings are also contraindicated for use in third degree burns and necrotic wounds. Gauze bandages, which are rendered non-adherent by incorporating petrolatum, still have a tendency to tear away new skin in removal and shed lint into the wound. In addition, they are non-absorbent. Hydrocolloids dressing are difficult to remove and malodorous yellow-brown drainage fluid typically collects under these dressings. Foams are not recommended for wounds with no exudates or wounds with dry eschar. Current hydrogel dressings have many advantages as compared to other products, but since they contain a large amount of water (80-90%), they are non-absorbent and not recommended for use on heavily exuding wounds, and if used alone, do not keep bacteria out of the wound.

This overview has been presented regarding wounds and different treatment modalities, and it is also important that a detailed description of polymer hydrogels be given since this invention pertains to hydrogel wound dressings and biomaterials.

A gel is a three-dimensional polymeric network that has absorbed a liquid to form a stable, usually soft and pliable, composition having a non-zero shear modulus. When the liquid absorbed by a gel is water, the gel is called a hydrogel. Water may comprise a significant weight percent of a hydrogel. This, plus the fact that many hydrogel-forming polymers are biologically inert, makes hydrogels particularly useful in a wide variety of biomedical applications.

For example, hydrogels are widely used in soft contact lens. They are also used as burn and wound dressings, with and without incorporated drugs that can be released from the gel matrix to aid in the healing process (e.g., see U.S. Pat. Nos. 3,063,685 and 4,272,518). Hydrogels have been used as coatings to improve the wettability of the surfaces of medical devices such as blood filters (U.S. Pat. No. 5,582,794). They have also found utility as devices for the sustained release of biologically active substances. For example, U.S. Pat. No. 5,292,515 discloses a method of preparing a hydrophilic reservoir drug delivery device. The '515 patent discloses that drug release rates can be controlled by changing the water content of the hydrogel subcutaneous implant, which directly affects its permeability coefficient.

In all the above applications, the gel or hydrogel is in bulk form, that is, it is an amorphous mass of material with no discernable regular internal structure. Bulk hydrogels have slow swelling rates due to the large internal volume relative to the surface area through which water must be absorbed. Furthermore, a substance dissolved or suspended in the absorbed water will diffuse out of the gel at a rate that depends on the distance it must travel to reach the surface of the gel. That is, molecules near the surface of the hydrogel will escape quickly, whereas molecules deeper within the matrix will take a much longer time to reach the outer surface of the gel. This situation can be ameliorated to some extent by using particulate gels. If each particle is sufficiently small, substances dispersed in the particles will diffuse to the surface and be released at approximately the same time.

Particulate gels can be formed by a number of procedures such as direct or inverse emulsion polymerization (Landfester, et al., Macromolecules, 2000, 33:2370) or they can be created from bulk gels by drying the gel and then grinding the resulting xerogel to particles of a desired size. The particles can then be re-solvated to form particulate gels. Particles having sizes in the micro ($10^{-6}$ meters (m)) to nano ($10^{-9}$ m) diameter range can be produced by this means. Molecules of a substance occluded by particles in these size ranges will all have about the same distance to travel to reach the outer surface of the particle and will exhibit near zero-order release kinetics. However, particulate gels have their problems. For instance, it is difficult to control the dissemination of the particles to, and localization at, a selected target site. Furthermore, while bulk hydrogels can be rendered shape-retentive, making them useful as biomaterials in a variety of medical applications, currently available particulate gels, cannot.

U.S. Pat. No. 7,351,430 B2 discloses a shape-retentive aggregate formed from hydrogel particles, thus combining the shape-retentiveness of bulk hydrogels with the substance release control of particulate gels. The '430 patent discloses a method of forming the shape-retentive aggregates comprising preparing a suspension of hydrogel particles in water or other polar liquid and concentrating the suspension until the particles coalesce into a shape-retentive aggregate held together by non-covalent bond physical forces including but not limited to hydrophobic/hydrophilic interactions and hydrogen bonds. The devices of this invention are particularly useful, for example, as drug delivery implants, tissue scaffolds for cartilage or bone repair, and moldable drug eluting contact lenses and catheters.

Co-pending U.S. Patent Application Publication No. US 2005/0118270A1 discloses a method of forming shape-retentive aggregates in situ, such that the shape of the aggregate would be dictated by the shape of the locus of application. Aggregate formation is accomplished by introducing a suspension of gel particles dispersed in a polar liquid, preferably water, wherein the gel particles have an absolute zeta potential enabling the particles to remain dispersed, into a receiving medium wherein the absolute zeta potential of the gel particles is reduced. The gel particles coalesce into a shape-retentive aggregate held together by non-covalent bond physical forces comprising hydrophobic-hydrophilic interactions and hydrogen bonding. Applications include, but not limited to biomedical uses such as joint reconstruction, wound repair, drug deliver implants formed in situ and cosmetic and reconstructive surgery.

DISCLOSURE OF THE INVENTION

Applicants disclose an integral, shape-conforming and shape-retentive aggregate that forms a dressing directly on a wound in situ and for other applications, forms a biomaterial in vivo in or on a wet bodily tissue. In the former application, the hydrogel nanoparticulate powder utilizes the blood or exudate from a wound, which is substantially composed of water and other biological compounds, such as serum, fibrin and white blood cells, absorbs this polar liquid and coalesces into a closely packed network of nanoparticles and wound fluid, held together by non-covalent bond physical forces comprising hydrophobic-hydrophilic interactions and hydrogen bonding. The aggregate dressings realize their characteristic wound conforming and shape-retentive properties by virtue of strong inter-particle attractive forces such as, without limitation, hydrogen bonds, and by virtue of hydrogen bonding between the particles and the liquid in the voids between the particles. The dressings remain intact as integral films during the healing stages of the wound, and fall off when the wound is no longer wet or healing has occurred. In the latter application, the powder utilizes any bodily fluid in vivo to form a shape-retentive aggregate biomaterial held together by the same forces previously described. The discussion to follow will primarily focus on wound dressings formed in situ, realizing however that the same properties can be provided for biomaterials formed in vivo for a wide array of medical applications.

One important feature of these dressings and biomaterials is that a variety of biological and/or pharmaceutical agents can be easily incorporated by mixing the nanoparticulate powder with an active or combination thereof and applying the mixed material to the wound site directly or placed in or on a wet bodily tissue in vivo. The resulting bandage will then provide a sustained delivery of the therapeutic compound(s) for a prolonged period of time to the underlying wound bed to aid in the treatment, management and eventual healing of the wound and/or to alleviate pain. The ability to form in situ protective, non-occlusive, biocompatible, shape-conforming, shape-retentive dressings with or without therapeutically active compounds for a variety of exuding wounds, such as burns, dermabrasions, skin donor sites, punch biopsies, decubitus and vascular ulcers and the like represents a major advancement in the treatment and management of wounds. These dressings have all of the ideal attributes that wound dressings should exhibit, namely provide adequate oxygen to the underlying tissue, since these non-occlusive dressing are porous as they are composed of nanoparticles and wound exudate, protect the wound from exogenous bacteria, eliminate the potential for infection by utilizing the exudate of the wound in the formation of the dressing, maintain a clean and moist environment as they are hydrogels and obtain complete wound closure.

Thus, the present invention provides a dry powder of polymeric nanoparticles prepared by a method by polymerizing an effective amount of a monomer or two or more monomers, at least one of which is a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate or a vicinyl epoxy (1C-4C) alkyl 2-alkenoate, in a polar liquid or a mixture of two or more miscible liquids, at least one of which is polar, and an effective amount of a surfactant to produce a suspension of a plurality of polymeric nanoparticles wherein the polymeric nanoparticles have an average diameter of less than $1\times10^{-6}$ m; and then removing the liquid(s) from the suspension such that the amount of liquid(s) remaining in the dry powder is less than 10% by weight wherein the percentage is based on the total weight of the dry powder.

In another aspect, the present invention provides a method of forming a shape-conforming, shape-retentive aggregate dressing in situ on a wet wound site by applying the dry powder to the wet wound site.

In a further aspect, the present invention provides a method of forming a shape-conforming, shape-retentive aggregate biomaterial in vivo in or on a wet bodily tissue, by applying the dry powder on the wet bodily tissue.

In another aspect, the present invention provides a method of treatment of a wound, comprising applying an effective amount of the dry powder.

BRIEF DESCRIPTION OF THE FIGURES AND TABLES

The patent or application file contains at least one drawing executed in color. Copies of this patent or patent application with color drawing(s) will be provided by the Office upon request and payment of the necessary fee.

Figure 1:
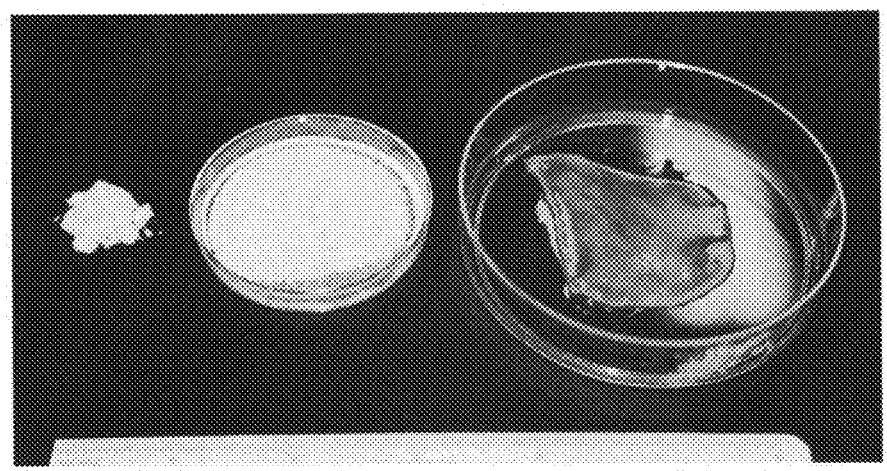
FIG. 1 is photograph showing the hydrogel nanoparticle powder, the powder applied to phosphate buffered saline and the resulting aggregate film after the powder hydrates.

Table 1 shows the ratios of HEMA and HPMA monomers in mass and mmol used to form hydrogel nanoparticles that consist of copolymers.

Table 2 shows the ratios of HEMA and GMA monomers used to form hydrogel nanoparticles that consist of copolymers.

Table 3 shows the relative elongation and tension at failure for aggregates formed of nanoparticles with different chemical compositions.

Table 4 shows the sizes of nanoparticles used to form aggregates of mixtures of nanoparticle with different chemical composition for the controlled release of 1,1-phenanthroline.

Modes for Carrying Out the Invention

Definitions

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

The term "polar liquid," as used herein has the meaning generally understood by those skilled in the chemical art. In brief, a polar liquid is one in which the electrons are unevenly distributed among the atoms of its molecules and therefore create an electrical dipole. To be polar, a molecule must contain at least one atom that is more electronegative than other atoms in the molecule. Examples of polar liquids include, without limitation, water, where the oxygen atom bears a partial negative charge and the hydrogen atoms a partial positive charge, and alcohols, wherein the O—H moiety is similarly polarized.

As used herein, "gel particle" refers to a microscopic or sub-microscopic quantity of a gel in a discrete shape, usually, but not necessarily, spherical or substantially so. As used herein, a "gel particle" includes small clusters of individual particles held together by non-covalent bond physical forces such as hydrophilic/hydrophobic interactions and hydrogen bonding, wherein the clusters do not adversely affect the stability of a gel particle suspension (suspension system) containing them or the performance of the nanoparticle powder in the methods of this invention. Clusters result from changes in concentration of gel particles in suspension and during the drying stage to isolate the nanoparticles. That is, at higher concentrations, it is more likely individual particles will get close enough to one another for non-covalent bond forces to cause them to coalesce.

As used herein, a "suspension" refers to a uniformly distributed, stable dispersion of a solid in a liquid in which the solid is not soluble. A surfactant may be added to the liquid to help stabilize the dispersion. As used herein, a "suspension system" refers to a suspension wherein gel particles of this invention are the dispersed solid. By "stable" is meant that the solid remains uniformly dispersed for at least 24 hours, unless subjected to disrupting external forces such as, without limitation, centrifugation or filtration.

As used herein, a "surfactant" has the meaning generally understood by those skilled in the chemical art. That is, a surfactant is a soluble compound, which may be anionic, cationic, zwitterionic, amphoteric or neutral in charge, and which reduces the surface tension of the liquid in which it is dissolved or that reduces interfacial tension between two liquids or a liquid and a solid.

As used herein, the term "shape-conforming and shape-retentive aggregate" refers to a structure formed in situ on a wet wound or biomaterial formed in vivo on or in a wet bodily tissue composed of a large number of gel particles held together by inter-particle and particle-liquid forces such as, without limitation, hydrophilic/hydrophobic interactions and hydrogen bonding wherein the structure maintains indefinitely as longs as it remains hydrated.

As used herein, the term "monomer" has the meaning understood by those skilled in the chemical art. That is, a monomer is a small chemical compound that is capable of forming a macromolecule of repeating units of itself, i.e., a polymer. Two or more different monomers may react to form a polymer in which each of the monomers are repeated numerous times, the polymer being referred to as a copolymer to reflect the fact that it is made up of more than one monomer.

As used herein, the term "size" when used to describe a gel particle of this invention refers to the volume of an essentially spherical particle as represented by its diameter, which of course is directly related to its volume. When referring to a plurality of gel particles, size relates to the average volume of the particles in the plurality as represented by their average diameter.

As used herein, the term "polydispersity" refers to the range of sizes of the particles in a suspension system. "Narrow polydispersity" refers to a suspension system in which the size of the individual particles, as represented by their diameters, deviates 10% or less from the average diameter of the particles in the system. If two or more pluralities of particles in a suspension system are both stated to be of narrow polydispersity, what is meant is that there are two distinct sets of particles wherein the particles of each set vary in diameter by no more than 10% from an average diameter of the particles in that set and the two averages are distinctly different. A non-limiting example of such a suspension system would be one comprising a first set of particles in which each particle has a diameter of 20 nm±10% and a second set of particles in which each particle has a diameter of 40 nm±10%.

As used herein, the term "broad polydispersity" refers to a suspension system in which the size of the individual particles of a set of particles deviates more than 10% from the average size of the particles of the set.

As used herein, the term "plurality" simply refers to more than one, i.e., two or more.

As used herein, "chemical composition" as it relates to a gel particle of this invention refers to the chemical composition of the monomers that are polymerized to provide the polymer strands of the particle, to the chemical composition and ratios of different monomers if two or more monomers are used to prepare the polymer strands of the particles and/or to the chemical composition and quantity of any cross-linking agent(s) that are used to inter-connect the particle strands.

As used in, a "particle strand" refers to a single polymer molecule or, if the system in which the strand exists contains a cross-linking agent, two or more inter-connected polymer molecules. The average number of polymer strands that will be cross-linked and the average number of cross-links between any two polymer strands in a particular gel particle will depend on the quantity of cross-linker in the system and on the concentration of polymer strands.

As used herein, a "working substance" refers to any substance that is occluded by a gel particle or entrapped in a shape-retentive aggregate dressing or biomaterial of this invention. Examples of working substances, without limitation, include biomedical agents; biologically active substances such as pharmaceutical agents, genes, proteins, peptides, poly-saccharides, growth factors, monoclonal antibodies, fragmented antibodies, antigens, polypeptides, DNA, RNA and ribozymes.

As used herein, the phrase "pharmaceutical agent" refers to both small molecule and to macromolecular compounds used as drugs. Among the former are, without limitation, antibiotics, chemotherapeutics (in particular platinum compounds and taxol and its derivatives), analgesics, antidepressants, anti-allergenics, anti-arrhythmics, anti-inflammatory compounds, CNS stimulants, sedatives, anti-cholinergics, anti-arteriosclerotics, and the like. Macromolecular compounds include, without limitation, monoclonal antibodies (mAbs), Fabs, proteins, peptides, cells, antigens, nucleic acids, enzymes, growth factors and the like. A pharmaceutical agent may be intended for topical or systemic use.

As used herein "hydroxy" refers to an —OH group.

As used herein, the term "alkyl" refers to a straight or branched chain saturated aliphatic hydrocarbon, i.e., a compound consisting of carbon and hydrogen only. The size of an alkyl in terms of how many carbon atoms it contains is indicated by the formula ("a"C-"b"C)alkyl where a and b are integers. For example, a (1C-4C)alkyl refers to a straight or branched chain alkyl consisting of 1, 2, 3 or 4 carbon atoms. An alkyl group may be substituted or unsubstituted.

As used herein, the term "alkoxy" refers to the group —O-alkyl wherein alkyl is as defined herein. The size of an alkoxy in terms of how many carbon atoms it contains is indicated by the formula ("a"C-"b"C) alkoxy where a and b are integers. For example, a (1C-4C) alkoxy refers to a straight or branched chain —O-alkyl consisting of 1, 2, 3 or 4 carbon atoms. An alkoxy group may be substituted or unsubstituted.

As used herein, "ester" refers to the group —C(O)O-alkyl wherein alkyl is as defined herein.

As used herein, "ether" refers to the group alkyl-O-alkyl wherein alkyl is as defined herein.

As used herein, "2-alkenoic acid" refers to the group $(R^1)(R^2)C=C(R^3)$—C(O)OH wherein each of $R^1$, $R^2$, $R^3$ are independently selected from hydrogen and alkyl wherein alkyl is as defined herein. These 2-alkenoic acids are exemplified, for example by, acrylic acid, methacrylic acid, etc.

As used herein, "2-alkenoate" refers to the group $(R^1)(R^2)C=C(R^3)$—C(O)O-alkyl wherein each of $R^1$, $R^2$, $R^3$ are independently selected from hydrogen and alkyl wherein alkyl is as defined herein.

As used herein, the phrases "voids between the hydrogel nanoparticles" or "between the nanoparticles" refer to the open space generated when essentially spherical gel particles touch at their circumferences when forming shape-retentive aggregate dressings of this invention. The volume of the voids can be approximated as 0.414 times the average radius of the spheres if the spheres have narrow polydispersity and pack in a close-packed arrangement.

As used herein, a "cross-linking agent" refers to a di-, tri-, or tetra-functional chemical entity that is capable of forming covalent bonds with functional groups on polymeric strands resulting in a three-dimensional structure.

A "hydrogen bond" refers to the electrostatic attraction between a hydrogen atom covalently bonded to a highly electronegative atom and another electronegative atom having at least one lone pair of electrons. The strength of a hydrogen bond, about 23 kJ (kilojoules) mol$^{-1}$, is between that of a covalent bond, about 500 kJ mol$^{-1}$, and a van der Waals attraction, about 1.3 kJ mol$^{-1}$. Hydrogen bonds have a marked effect on the physical characteristics of a composition capable of forming them. For example, ethanol has a hydrogen atom covalently bonded to an oxygen atom, which also has a pair of unshared (i.e., a "lone pair") electrons and, therefore, ethanol is capable of hydrogen bonding with itself. Ethanol has a boiling point of 78° C. In general, compounds of similar molecular weight are expected to have similar boiling points. However, dimethyl ether, which has exactly the same molecular weight as ethanol but which is not capable of hydrogen bonding between molecules of itself, has a boiling point of −24° C., almost 100 degrees lower than ethanol. Hydrogen bonding between the ethanol molecules has made ethanol act as if it were substantially higher in molecular weight.

As used herein, an "excipient" refers to an inert substance added to a pharmaceutical composition to facilitate its administration. Examples, without limitation, of excipients include calcium carbonate, calcium phosphate, various sugars and types of starch, water-soluble polymers, cellulose derivatives, gelatin, vegetable oils and polyethylene glycols. A "pharmaceutically acceptable excipient" refers to an excipient that does not cause significant irritation to an organism and does not abrogate the biological activity and properties of the administered compound.

As used herein, the phrase "useful in the treatment of" means that the pharmaceutical agent is known to either directly or indirectly inhibit, preferably destroy or deactivate, the causal agent of the disease indicated or to at least ameliorate, preferably eliminate, the symptoms of that disease. With regard to wound healing, the agent is known to at least decrease the time to wound closure.

As used herein, the term "cancer" refers to malignant neoplasms, which, in turn relate to a large group of diseases that can arise in virtually any tissue composed of potentially dividing cells. The basic characteristic of cancer is a transmissible abnormality of cells that is manifested by reduced control over growth and function leading to serious life-threatening effects on the host through invasive growth and metastases.

As used herein, "ocular disease" refers to a disease in which the eyes do not function properly so that vision is affected. Examples of ocular diseases include, without limitation, glaucoma, macular degeneration, diabetic retinopathy, and cataracts. Examples of pharmaceutical agents useful in the treatment of ocular diseases include, without limitation, anti-inflammatory agents, antibiotics, antimicrobials and pressure reducing agents.

As used herein, an "infection" refers to a disease state caused by a microorganism such as, without limitation, a bacterium, a virus, a prion, a fungus, an amoeba or a protozoon. Examples of pharmaceutical agents useful in the treatment of infections include, without limitation antimicrobials, antibiotics and bacteriostatic agents.

The shape-retentive aggregate dressings or biomaterials of this invention may be manipulated using the disclosures herein so as to be capable of occluding and/or entrapping virtually any pharmaceutical agent presently known, or that may become known, to those skilled in the art as being effective in the treatment and/or prevention of any of the above diseases and all such pharmaceutical agents are within the scope of this invention.

As used herein, the term "about" means±15% of the value modified with the term.

As used herein, the term "in situ" refers to the process or procedure of forming a wound dressing directly in place on or in a mammal, in particular a human being.

As used herein, the term "biomaterial" refers to the shape-retentive and shape-conforming material formed when hydrogel nanoparticle powder is introduced in vivo to a wet wound tissue in a mammal, in particular a human being.

As used herein, the term "hydrophilic/hydrophobic interactions" refers to the inter- or intra-molecular association of chemical entities through physical forces, whereby hydrophilic compounds or hydrophilic regions of compounds tend to associate with other hydrophilic compounds or hydrophilic regions of compounds, and hydrophobic compounds or hydrophobic regions of compounds tend to associate with other hydrophobic compounds or hydrophobic regions of compounds.

As used herein, the term "occlude" has the meaning generally understood by those skilled in the chemical art, that is, to absorb and retain a substance for a period of time. With regard to this invention, substances may be absorbed by and retained in, i.e. occluded by, gel particles of this invention during their formation.

As used herein, the term "entrapped" refers to the retention for a period of time of a substance in the voids between the gel particles comprising shape-retentive aggregate dressings or biomaterials of this invention.

As used herein, the term "average molecular weight" refers to the weight of individual polymer strands or cross-linked polymer strands of this invention. For the purpose of this invention, average molecular weight is determined by gel permeation chromatography with laser light scattering detection.

As used herein, "growth factors" refer to certain polypeptides that, when bound by growth factor receptors on the surface of cells, stimulate the cells to grow in size and to divide. Growth factor receptors are specific to each growth factor so that only cells that express the exact receptor for a particular growth factor will be stimulated by that growth factor. Examples of growth factors include, without limitation, vascular endothelial growth factor (VEGF), insulin-like growth factor (IGF), fibroblast growth factor (FGF), epidermal growth factor (EGF), hepatocyte growth factor (HGF) and platelet-derived growth factor (PDGF).

As used herein, "tissue scaffold" refers to a highly porous, artificial, three-dimensional extra-cellular matrix that is used in vivo as a framework to which cells can attach and grow to regenerate tissues lost through injury or disease.

As used herein, "wet wound" refers to any wound in which fluid is exiting the wound site, which may be blood or exudate.

As used herein, "bodily fluid" refers to any liquid present in the bodily tissues of mammals, preferably man.

As used herein, "exudate" refers to the fluid present in a wound site substantially composed of water and other biological materials, such as white blood cells, fibrin, and serum.

As used herein, "working substance/particulate powder composite" refers to a mixture of the nanoparticle dry powder and any working substance and/or pharmaceutical excipient.

EMBODIMENTS

This invention provides a dry powder of polymeric nanoparticles; methods of forming a shape-conforming, shape-retentive aggregate dressing in situ on a wet wound site; methods of forming a shape-conforming, shape-retentive aggregate biomaterial in vivo in or on a wet bodily tissue and uses of the dry powder in the treatment of wounds. These and further embodiments are discussed below in details.

In an embodiment, this invention provides a dry powder of polymeric nanoparticles prepared by polymerizing an effective amount of a monomer or two or more monomers, at least one of which is a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate or a vicinyl epoxy (1C-4C) alkyl 2-alkenoate, in a polar liquid or a mixture of two or more miscible liquids, at least one of which is polar, and an effective amount of a surfactant to produce a suspension of a plurality of polymeric nanoparticles wherein the polymeric nanoparticles have an average diameter of less than $1\times10^{-6}$ m. After polymerization, the liquid(s) are from the suspension such that the amount of liquid(s) remaining in the dry powder is less than 10% by weight wherein the percentage is based on the total weight of the dry powder.

In some embodiments, the gel particles of the methods described above have an average diameter of from about 1 nanometer to about 1 micrometer, while in others the gel particles have an average diameter of from about 20 to about 800 nanometers. In alternative embodiments, the average diameter of the gel particles is from about 100 to about 700 nanometers, or alternatively from about 40 to about 300 nanometers, or alternatively from about 100 to about 800 nanometers, or alternatively from about 300 to about 800 nanometers, or alternatively from about 600 to about 800 nanometers, or alternatively from about 50 to about 700 nanometers. In a yet further embodiments, the average diameter of the gel particles is greater than about 35 nanometers, or yet further 55 nanometer, or yet further greater than about 75 nanometers, or yet further greater than about 100 nanometers, or yet further greater than about 150 nanometers, or yet further greater than about 200 nanometers, or yet further greater than about 250 nanometers, 300 nanometers, or yet further greater than about 350 nanometers, or yet further greater than about 400 nanometers.

In some embodiments, the gel particles of the methods described above, are about the same average diameter, are formed from one or more monomers and are of a narrow polydispersity. In some embodiments, the plurality of gel particles of the methods described above is at a concentration in the range of 5-20% that results in cluster formation. Alternative concentrations within the scope of this invention include the range of about 5-10%, or alternatively about 5-15%, or alternatively about 10-20%, or alternatively about 15-20%, or alternatively about 10-15%, or alternatively about 6-19%, or alternatively about 7-18%, each of which results in cluster formation. In some embodiments, the pluralities of gel particles of the methods described above, are of differing average diameter, are formed from one or more monomers and are of a narrow polydispersity while in others they are of a broad polydispersity.

In another embodiment, the dry powder is obtained by adding one or more first working substance(s) in an amount effective to give a first working substance-containing liquid, wherein after polymerization, a portion of the first working substance-containing liquid is occluded by the polymeric nanoparticles and then adding one or more second working substance(s) in an effective amount to the dry polymeric nanoparticles and dry blending to give a second working substance-containing particulate powder, wherein the first working substance(s) may be the same as or different than the second working substance(s).

In another embodiment, the dry powder is obtained by adding from 0.01 to 10 mol percent of a surfactant to a polymerization system comprising a monomer, or two or more different monomers, wherein the monomer or at least one of the two or more monomers comprise(s) one or more hydroxy and/or one or more ester groups, in a polar liquid or mixture of polar liquids, wherein the polar liquid or at least one of the two or more polar liquids comprise(s) one or more hydroxy groups and polymerizing the monomer(s) to form a plurality of polymeric nanoparticles, each particle comprising a plurality of polymer strands, wherein the addition is in the absence of a cross-linking agent and the resulting non-cross-linked polymer or copolymer is water insoluble but water swellable, and drying the nanoparticles to obtain the dry powder. In alternative embodiments, the effective amount of the surfactant is from about 0.01 weight percent to about 0.1 weight percent, or alternatively from about 0.01 weight percent to about 0.2 weight percent, or alternatively from about 0.01 weight percent to about 0.3 weight percent, or alternatively from about 0.01 weight percent to about 0.4 weight percent, or alternatively from about 0.1 weight percent to about 1.0 weight percent, or alternatively from about 0.1 weight percent to about 3.0 weight percent, or alternatively from about 0.1 weight percent to about 5.0 weight percent, or alternatively from about 0.1 weight percent to about 7.0 weight percent, or alternatively from about 0.1 weight percent to about 9.0 weight percent, or alternatively from about 0.02 weight percent to about 9.5 weight percent.

In another embodiment, the monomer(s) for the process described above, are selected from the group consisting of a 2-alkenoic acid, a hydroxy(2C-4C)alkyl 2-alkenoate, a dihydroxy(2C-4C) alkyl 2-alkenoate, a hydroxy(2C-4C)alkoxy(2C-4C)alkyl 2-alkenoate, a (1C-4C)alkoxy(2C-4C)alkoxy(2C-4C)alkyl 2-alkenoate and a vicinyl epoxy(1C-4C)alkyl 2-alkenoate and a combination of two or more thereof. In a further embodiment, the monomer(s) are selected from the group consisting of acrylic acid, methacrylic acid, 2-hydroxyethyl acrylate, 2-hydroxyethylmethacrylate, diethyleneglycol monoacrylate, diethyleneglycol monomethacrylate, 2-hydroxypropyl acrylate, 2-hydroxypropyl methyacrylate, 3-hydroxypropyl acrylate, 3-hydroxypropyl methacrylate, dipropylene glycol monoacrylate, dipropylene glycol monomethacrylate, 2,3-dihydroxypropyl methacrylate, glycidyl acrylate, glycidyl methacrylate and a combination of two or more thereof. In another embodiment, the monomer(s) are selected from the group comprising methacrylic acid, 2-hydroxyethyl methacrylate, 2-hydroxypropyl methacrylate, 3-hydroxypropyl methacrylate, glycerol methacrylate and a combination of two or more thereof.

In another embodiment, the liquid(s) for the process described above, are selected from the group consisting of water, a (1C-10C) alcohol, a (2C-8C)polyol, a (1C-4C)alkyl ether of a (2C-8C)polyol, a (1C-4C)acid ester of a (2C-8C)polyol, a hydroxy-terminated polyethylene oxide, a polyalkylene glycol and a hydroxy(2C-4C)alkyl ester of a mono, di- or tricarboxylic acid. In a further embodiment, the liquid(s) are selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hydroxyethyl)citrate, di(hydroxypropyl)oxalate, glyceryl diacetate, and glyceryl monobutyrate. In a particular embodiment, the liquid is water.

In another embodiment, the dry powder is obtained by a process comprising adding from 0.01 to 10 mol percent of a surfactant to a polymerization system comprising a monomer, or two or more different monomers, wherein the monomer or at least one of the two or more monomers comprise(s) one or more hydroxy and/or one or more ester groups, in a polar liquid or mixture of polar liquids, wherein the polar liquid or at least one of the two or more polar liquids comprise(s) one or more hydroxy groups; adding from 0.01 to 10 mol percent of a surfactant to the polymerization system; polymerizing the monomer(s) to form a plurality of gel nanoparticles, each particle comprising a plurality of polymer strands, such that the resulting non-cross-linked polymer or copolymer is water insoluble but water swellable and drying the nanoparticles to obtain the dry powder, wherein the process further comprises adding from about 0.1 to about 15% mol percent of a cross-linking agent to the polymerization system which results in cross-linking of the polymer strands. The cross-linking agent is selected from the group consisting of ethylene glycol diacrylate, ethylene glycol dimethacrylate, 1,4-dihydroxybutane dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, diallyl tartrate, diallyl malate, divinyl tartrate, triallyl melamine, N,N'-methylene bisacrylamide, diallyl maleate, divinyl ether, 1,3-diallyl 2-(2-hydroxyethyl)citrate, vinyl allyl citrate, allyl vinyl maleate, diallyl itaconate, di(2-hydroxyethyl)itaconate, divinyl sulfone, hexahydro-1,3,5-triallyltriazine, triallyl phosphite, diallyl benzenephosphonate, triallyl aconitate, divinyl citraconate, trimethylolpropane trimethacrylate and diallyl fumarate.

In another embodiment, the cross-linked polymer strands have an average molecular weight of from about 3,000 to about 2,000,000. In alternative embodiments, the cross-linked polymer strands have an average molecular weight of from about 3,000 to about 200,000, or alternatively from about 3,000 to about 20,000, or alternatively from about 30,000 to about 2,000,000, or alternatively from about 300,000 to about 2,000,000, or alternatively from about 100,000 to about 1,000,000, or alternatively from about 50,000 to about 1,500,000.

In another embodiment, the process described above further comprises adding an effective occluding amount of one or more working substance(s) to the polar liquid(s) of the polymerization system prior to polymerization. In another embodiment, the effective amount of the working substance-containing gel nanoparticles occlude from about 0.1 to about 90 weight percent working substance(s)-containing liquid. In alternative embodiments, the effective amount of the working substance-containing gel particles occlude from about 1 to about 90 weight percent working substance-containing liquid, or alternatively from about 10 to about 90 weight percent, or alternatively from about 0.1 to about 70 weight percent, or alternatively from about 0.1 to about 50 weight percent, or alternatively from about 0.1 to about 20 weight percent, or alternatively from about 10 to about 50 weight percent.

In another embodiment, the method comprises adding an effective amount of one or more first working substance(s) to the polymerization system to give a first working substance-containing liquid, wherein after polymerization, a portion of the first working substance-containing liquid is occluded by the polymeric nanoparticles; and adding an effective amount of one or more second working substance(s) to the particulate powder and dry blending to give a second working substance-containing particulate powder, wherein the first working substance(s) may be the same as or different than the second working substance(s). In a further embodiment, from 0.1 to 90 weight percent of the first working substance(s) is occluded by the plurality of hydrogel particles and from 0.1 to 90 weight percent of the second working substance(s) is entrapped between the nanoparticles.

In another embodiment, one or more working substance(s) is added to the dry powder and blending to provide a working substance(s)/particulate powder composite. In another embodiment, the working substance(s)/particulate powder composite contains from about 1 to 90 weight percent of working substance(s).

In another embodiment, the working substance(s) comprise one or more biomedical agent(s), which may be the same or different. In another embodiment, the biomedical agent(s) comprise(s) cells, platelets or one or more tissue-growth scaffold materials. In a further embodiment, one or more of the biomedical agent(s) comprise(s) one or more pharmaceutical agent(s). In another embodiment, the pharmaceutical agent(s) further comprises/comprise one or more pharmaceutically acceptable excipient(s). In a further embodiment, the pharmaceutical agent(s) comprises/comprise a peptide, a protein or a poly-saccharide. In another embodiment, the pharmaceutical agent(s) is/are useful for the treatment of wounds, cancer, pain, infection or diseases of the eye. In another embodiment, the pharmaceutical agent(s) is/are growth factors.

In another embodiment, the method further comprises adding one or more pharmaceutically acceptable excipients to the dry powder. In an embodiment, one or more pharmaceutically acceptable excipients are from about 1 to about 50 weight percent of the dry powder. In alternative embodiments, one or more pharmaceutically acceptable excipients is from about from about 10 to about 50 weight percent weight percent of the dry powder, or alternatively from about 20 to about 50 weight percent, or alternatively from about 30 to about 50 weight percent, or alternatively from about 40 to about 50 weight percent, or alternatively from about 1.0 to about 40 weight percent, or alternatively from about 1.0 to about 30 weight percent, or alternatively from about 1.0 to about 20 weight percent, or alternatively from about 1.0 to about 10 weight percent, or alternatively from about 5.0 to about 45 weight percent.

In another embodiment, the pharmaceutically acceptable excipient(s) is/are a water soluble filler material(s).

The invention also provides a method of forming a shape-conforming, shape-retentive aggregate dressing in situ on a wet wound site by applying a dry powder of polymeric nanoparticles to the wet wound site wherein the dry powder comprises a plurality of gel particles having an average diameter of less than $1 \times 10^{-6}$ m, wherein the gel particles comprise an effective amount of a plurality of polymeric strands obtained by polymerization of an effective amount of a monomer or two or more monomers, at least one of which is a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate or a vicinyl epoxy (1C-4C) alkyl 2-alkenoate, in a polar liquid or a mixture of two or more miscible liquids, at least one of which is polar, and an effective amount of a surfactant to stabilize the plurality of gel particles.

In another embodiment, this invention provides a method of forming a shape-conforming, shape-retentive aggregate biomaterial in vivo in or on a wet bodily tissue, by applying a dry powder of polymeric nanoparticles to the wet bodily tissue wherein the dry powder comprises a plurality of gel particles having an average diameter of less than 1×10-6 m, wherein the gel particles comprise an effective amount of a plurality of polymeric strands obtained by polymerization of an effective amount of a monomer or two or more monomers, at least one of which is a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate or a vicinyl epoxy (1C-4C) alkyl 2-alkenoate, in a polar liquid or a mixture of two or more miscible liquids, at least one of which is polar, and an effective amount of a surfactant to stabilize the plurality of gel particles. The polymeric nanoparticles absorb bodily fluid and coalesce into a shape-conforming biomaterial held together by non-covalent forces comprising hydrophilic-hydrophobic particle interactions and hydrogen bonding between the particles and the bodily fluid in the voids between the particles.

The compositions of this invention are useful to treat wounds by applying the dry powder of polymeric nanoparticles prepared by a method comprising polymerizing an effective amount of a monomer or two or more monomers, at least one of which is a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate or a vicinyl epoxy (1C-4C) alkyl 2-alkenoate, in a polar liquid or a mixture of two or more miscible liquids, at least one of which is polar, and an effective amount of a surfactant and lyophilizing for removal of liquids such that the amount of liquid remaining in the polymeric nanoparticles is less than 10% w/w. In a further embodiment, the dry powder further comprises one or more tissue-growth scaffold materials or pharmaceutical agent(s). In a further embodiment, the dry powder further comprises collagen, hyaluronic acid, pharmaceutical agent(s) useful for the treatment of wounds, for the treatment of cancer, for the treatment of pain, for the treatment of ocular disease, or the pharmaceutical agent(s) that are growth factors and antibiotics. In a further embodiment, the pharmaceutical agent is lidocaine, erythromycin, doxycycline or rifampin. In a further embodiment, the pharmaceutical agents are VEGF and PDGF polypeptides.

The wound dressings and biomaterials of this invention can be formed by first polymerizing specific monomers in a suspension system comprising a liquid or a mixture of polar, miscible liquids and a surfactant resulting in discrete gel nanoparticles, wherein the particles are then purified, isolated, dried and applied to a wet wound forming in situ dressings that are integral, shape-conforming and shape-retentive. The unique chemical and physical properties of these hydrogel nanoparticles absorb some of the blood or exudate from the wound, causing them to coalesce and be held together as an integral dressing. That is, the particles of this invention, once exposed to a polar liquid such as blood or exudate, which is primarily water, white blood cells, fibrin, and other biological compounds, absorb some of the fluid, coalesce and are held together by strong inter-particle and particle-liquid interactions such as, without limitation, hydrophobic-hydrophilic interactions and hydrogen bonding, the latter by virtue of the fact that the at least one of the monomers used to produce the polymer strands that make up the gel particle of this invention must comprise one or more hydroxy groups and/or one or more ester groups. In addition, some of the non-absorbed exudate remains trapped in the void spaces between the particles after they coalesce, and since the exudate is a polar material, strong hydrogen bonding occurs between the particles and the exudate. An important requirement for the formation of the wound dressings in situ using dry, nanoparticulate powder is that the wound site must be wet, that is wound fluid must be present otherwise particle aggregation cannot occur in situ.

However, it is also possible to form a shape-retentive aggregate wound dressing, with or without a medicinal agent, on a bodily tissue that is not wet or releasing a minimum amount of exudate. In this case, using the teachings of the previous cited U.S. Patent Application Publ. No.: US 2004/0086548A1 and the teachings of this invention disclosure, the dry nanoparticulate powder is mixed with a polar liquid or mixture thereof and immediately applied to a bodily tissue. The nanoparticles coalesce into a shape-retentive and shape-conforming aggregate dressing, by virtue of the strong particle-particle and particle-liquid interactions as previously discussed. The only requirements to utilize these types of dressings is that the polar solvent or mixtures thereof are safe, non toxic and approved by the FDA for topical and systemic applications.

In addition, one can also add a volatile solvent to a mixture of the dry nanoparticle powder and polar, plasticizing liquid or mixture thereof, homogenize the components and package the resulting mixture in a sealable container to prevent evaporation of the solvent. Upon application to a non-exuding wound surface or intact skin, the volatile solvent evaporates leaving a shape-retentive aggregate dressing on the application site.

The gel nanoparticles are prepared in a polymerization system that consists of one or more monomers selected generally from those monomers that, on polymerization, provide a polymer that is water insoluble, whether crosslinked or not, and capable of hydrogen bonding. General classes of monomers that have this capability include, without limitation, a hydroxy(2C-4C)alkyl 2-alkenoate, a dihydroxy(2C-4C) alkyl 2-alkenoate, a hydroxy(2C-4C)alkoxy(2C-4C)alkyl 2-alkenoate, a (1C-4C)alkoxy(2C-4C)alkoxy(2C-4C)alkyl 2-alkenoate and a vicinyl epoxy(1C-4C)alkyl 2-alkenoate and combinations thereof.

The monomers include 2-hydroxyethyl acrylate, 2-hydroxyethyl methacrylate, diethylene glycol monoacrylate, diethylene glycol monomethacrylate, 2-hydropropyl acrylate, 2-hydroxypropyl methacrylate, 3-hydroxypropyl acrylate, 3-hydroxypropyl methacrylate, glycerol methacrylate, dipropylene glycol monomethacrylate, dipropylene glycol monoacrylate, glycidyl methacrylate, 2,3-dihydroxypropyl methacrylate, and mixtures thereof. Particular monomers are 2-hydroxyethyl methacrylate (HEMA), 2-hydroxypropyl methacrylate, 3-hydroxypropyl methacrylate, and glycerol methacrylate.

Co-monomers that are not capable of hydrogen bonding may be added to the polymerization system to modify the physical and chemical characteristics of the resulting gel particles. Examples of co-monomers that may be used in conjunction with the above monomers are, without limitation, acrylamide, N-methylmethacrylamide, N,N-dimethacrylamide, methylvinylpyrrolidone, N,N-dimethylaminoethyl methacrylate N,N-dimethylaminoethyl acrylate. Other co-monomers capable of hydrogen bonding, without limitation, such as acrylic acid and methacrylic acid may also be added to the polymerization system to modify the ionic character and pH of the resulting gel nanoparticles if desired.

In addition, non-polymerizing additives such as, without limitation, alkyl alkanoates as exemplified by methyl butyrate, butyl acetate, etc. may be added to the polymerization reaction to further modify the physical and chemical characteristics of the resulting gel particles.

A cross-linking agent also may be added to the polymerization system to strengthen the three-dimensional structure of the resulting gel particles. The cross-linking agent can be non-degradable, such as, without limitation, ethylene glycol diacrylate or dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, triallyl melamine, N,N'-methylene bisacrylamide, diallyl maleate, divinyl ether, diallyl monoethylene glycol citrate, vinyl allyl citrate, allyl vinyl maleate, divinyl sulfone, hexahydro-1,3,5-triallyltriazine, triallyl phosphite, diallyl benzene phosphonate, a polyester of maleic anhydride with triethylene glycol, diallyl aconitrate, divinyl citraconate, trimethylolpropane trimethacrylate and diallyl fumarate. Other non-degradable cross-linking agents will become apparent to those skilled in the art based on the disclosures herein and are within the scope of this invention.

The chemical composition of the polymers making up the individual gel particles comprising the resulting wound dressing aggregates formed in situ are stable and do not readily degrade under a wide range of environmental or physiological conditions. The aggregate dressings formed in situ remain in place until the wound heals and/or the wound dries out. On the other hand, the aggregate dressings and/or biomaterials formed in vivo can be designed, based on the specific application, such they will lose strength or integrity under selected conditions in a controllable fashion. For example, without limitation, by selecting appropriate additives, they can be entrapped in the aggregate matrix as it is being formed such that the resulting aggregate dressings will become more porous as the additive(s) change(s) structure, composition and/or reactivity upon exposure to variety of environmental and/or physiological conditions.

When the liquid for use in the polymerization system of this invention is water, the particles are hydrogel particles.

Certain organic liquids may also be used in the polymerization system of this invention. In general, they should have boiling points above about 60° C., or alternatively above about 80° C., 100° C., 120° C., 140° C. 160° C., 180° C. or about 200° C. Presently organic liquids that may be used are biologically inert, non-toxic, polar, water-miscible organic liquids such as, without limitation, ethylene glycol, propylene glycol, dipropylene glycol, butanediol-1,3, butanediol-1,4, hexanediol-2,5,2-methyl-2,4-pentanediol, heptanediol-2,4,2-ethyl-1,3-hexanediol, diethylene glycol, triethylene glycol, tetraethylene glycols, and the higher polyethylene glycols and other water-soluble oxyalkylene homopolymers and copolymers having a molecular weight up to about 2000, preferably up to about 1600. For example, without limitation, hydroxy-terminated polymers of ethylene oxide having average molecular weights of 200-1000, water-soluble oxyethyleneoxypropylene polyol (especially glycol) polymers having molecular weights up to about 1500, preferably up to about 1000, monoacetin, glycerine, tri(hydroxyethyl)citrate, ethylene glycol monomethyl ether, di(hydroxypropyl)oxalate, hydroxypropyl acetate, glyceryl triacetate, glyceryl tributyrate, liquid sorbitol ethylene oxide adducts, liquid glycerine ethylene oxide adducts, diethylene glycol monoethyl ether, and ethylene glycol diacetate, may be used.

In an embodiment of this invention, hydrogel particles, having nominal sizes in the $10^{-9}$ meters to the $10^{-6}$ m range are produced by redox, free radical or photo-initiated polymerization in water containing a surfactant. In this manner, particles of relatively narrow polydispersity can be produced. If, for a particular application, such as, without limitation, release of biologically active substances over an extended period of time is desired, it may be advantageous to produce and isolate particles of broad polydispersity that comprise a medicated wound dressing formed in situ or therapeutic biomaterial produced in vivo.

If, on the other hand, the goal is sequential release of a drug or burst release at different times rather than continuous release, two or more groups of particles of different sizes but narrow polydispersity within each size may be used. For example, without limitation, gel particles of different sizes but narrow polydispersity may be formed using the techniques described herein in separate polymerization systems that contain a particular biologically active substance. The substance-containing particles, after isolation and drying, may then be combined as a single powder and applied to a wound to produce a medicated shape-retentive dressing. Due to the difference in size of the particles, the biologically active substance will be burst-released at different times. Similarly, using the same technique but adding a first biologically active substance to one of the polymerization systems and a different biologically active substance to the second polymerization system will result in particles that will release their particular active substance at different times, i.e., sequential release.

Biologically active substances can also be introduced to the wound dressings and biomaterials described in this invention by mixing isolated and dried nanoparticles with these various active substances. After application to a wet wound, the dressing forms in situ and some of the active(s) is trapped between the void spaces between the particles comprising the dressing. These actives will be released from the dressing over a prolonged period of time, to enhance wound healing, and the release rate(s) will be affected by the physical properties of the active, such as molecular weight and water solubility, in addition to the size of the nanoparticles comprising the dressing. It is clear to one skilled in the art that a variety of medicated dressings and/or biomaterials can be produced, for example, using dry nanoparticles of various sizes containing occluded actives in combination with or without other biologically active compounds that are blended together in powder form and applied to a wound, and all such dressings are within the scope of this invention disclosure.

Numerous factors will affect the chemical and physical characteristics of the aggregates of this invention. One is the molecular weight of the polymer used to form the individual hydrogel nanoparticles. It has been found that hydrogel particles consisting of low molecular weight polymers will generally not form stable, strong aggregate wound dressings in situ. Thus, higher molecular weight polymers are used in this invention. While the use of cross-linking agents can ameliorate some of the problems associated with low molecular weight polymers, too much cross-linking agent may be detrimental. If the hydrogel particles contain a large amount of cross-linking agent and/or if the cross-linking agent is highly hydrophobic, the resulting polymeric network may not permit optimal absorption and occlusion of blood or exudate resulting in less desirable wound dressings. So, the polymers that comprise the gel particles of this invention have molecular weights in the range of about 3,000 to about 2,000,000 Da. This may be accomplished by selecting an appropriate commercial monomer, by using a polymerization system that gives polymers of in the desired molecular weight range or by including a cross-linker in the polymerization system to join together short polymer strands to reach the desired molecular weight range.

Particle size will also affect the characteristics of the aggregate wound dressings. It has been determined that smaller gel particles will generally absorb and trap liquid more easily and faster due to surface area and will give a more resilient dressing matrix. Gel particles having sizes, again as characterized by their average diameters, in the range of about 1 to about 1,000 nm, or alternatively from about 10 to about 800 nm, can be used.

If a cross-linking agent is used, its chemical composition and the amount used, i.e., the resulting cross-linking density, will affect the characteristics of the particles as previously discussed and thereupon will affect the characteristics of the wound dressings formed. For example, too much crosslinker would provide polymer strands of a higher molecular weight, however may also create too much hydrophobic character and hydrophobic domains throughout the hydrogel nanoparticles, thus preventing the critical strong inter-particle and particle-liquid interactions such as, without limitation, hydrophobic-hydrophilic interactions and hydrogen bonding to occur during the formation of the wound dressings prepared in situ on a wound or biomaterials formed in vivo. The amount of cross-linking agent used in preparing gel particles of this invention is preferably in the range of about 0.001 to about 10, preferably about 0.1 to about 2 mol percent of monomer.

The chemical composition and amount of surfactant present in the isolated, dry nanoparticle powder will affect the aggregation rate when exposed to a polar liquid and the physical and chemical characteristics of the resulting aggregate wound dressings of this invention. During the isolation process, a certain amount of surfactant is required to prevent self aggregation of the particles as they become concentrated during the drying cycle. However, too much surfactant would prevent the dry particles from forming optimum wound dressing aggregates upon exposure to blood, wound exudate or other polar liquids. The amount of surfactant present in the nanoparticulate powder is preferably in the range of about 0.1 to 6 weight percent of the nanoparticle powder. It is also important to note that the isolation and drying processes performed on these gel nanoparticles must be such to prevent or minimize the particles from concentrating and self-aggregating, at which point the strong particle-particle and particle-liquid interactions overpower the inherent ability for the surfactant to keep the particles from coalescing. Isolation and drying processes such as spray drying and lyophilization are used, whereas direct evaporation is not since self-aggregation occurs extensively and the resulting dry powder will not form a viable dressing in situ when applied to a wet wound site. It is clear to one skilled in the art that other isolation and drying processes can be used as long as self-aggregation is minimized or prevented. The various parameters discussed above are, of course, inter-dependent.

In one embodiment of this invention, hydrogel nanoparticles are produced by polymerizing non-ionic monomers in water containing a surfactant. The suspension of hydrogel particles is treated to remove unreacted monomer and other impurities. The particles are isolated, dried and the particulate powder is applied to a wound or to a bodily tissue in vivo, which absorbs some exudates, blood or other bodily fluid and coalesces into a shape-retentive, shape-conforming wound dressing or biomaterial. The dressing remains integral and shape-retentive by virtue of the strong inter-particle—and particle-liquid interactions such as, without limitation, hydrophobic-hydrophilic interactions and hydrogen bonding. That is, by applying the nanoparticle hydrogel powder into a medium of higher ionic strength, e.g. PBS, serum, wound exudate or other bodily fluid, the particles self-assemble into a compact elastic, shape-retentive aggregate dressing. In an embodiment, the medium is in vivo, that is, a bodily tissue, and the shape-retentive aggregate assumes and retains the shape of the region of the body into which the powdered is applied. If the medium is ex vivo, it may be, without limitation, be further pressure-shaped, extruded, or molded into a desired shape, which it will retain so long as the aggregate is maintained in the hydrated state.

The aggregate wound dressings of this invention have many applications including, without limitation, delivery of a biologically active substance or substances to a predetermined location such as a wound site. The target may be veterinary, involving delivery of medicaments to animals such as reptiles, mammals and birds. In particular, the target may be a human involving the controlled, directed delivery of pharmaceutical agents to the patient.

Another embodiment of this invention involves dissolving or suspending the biologically active agent in the polymerization system prior to polymerization. As the polymerization reaction proceeds and hydrogel nanoparticles form, liquid containing the biologically active substance is occluded by the forming particles. Un-occluded biologically active agent is then removed when the particles are treated to remove excess monomer and surfactant. The suspension of biologically active substance-containing particles is then isolated and dried to produce nanoparticulate powder. The drying process is done by traditional means including, without limitation, spray drying and lyophilization. The powder may then be introduced either ex vivo or in vivo, in the latter case introduction preferably being by applying the powder to a wound site whereupon the particles coalesce into a shape-retentive, shape-conforming aggregate medicated dressing.

It is also an embodiment of this invention to remove non-occluded biologically active agent from the suspension system along with the excess monomer and with the surfactant, isolate and dry the nanoparticles containing the occluded biologically active agent, and then add an entirely different biologically active substance to the nanoparticulate powder prior to forming a wound dressing in situ so as to entrap the latter during aggregate formation. The substance entrapped in the voids in the aggregate will normally be released at a very different rate from the substance occluded by the particles. In this manner, a broad range of delivery rates can be achieved. Diversity in delivery profile can also be achieved by varying the chemical composition and particle size of the individual hydrogel particles comprising the wound dressing aggregates.

If the biomaterial aggregate is produced in vivo, a certain amount of biologically active substance will be entrapped in the void spaces between the particles, depending upon the physical properties such as type and size of the biologically active substance and the rate of aggregate formation. The rate of aggregate formation is a function of the particle size and composition of the gel nanoparticles, the type and amount of surfactant or combination of surfactants present in the dry nanoparticulate powder, the polar medium to which the powder is applied and the temperature of the medium.

In addition to the above, other water soluble substances may be added to the dry gel nanoparticles of this invention to alter the aggregation and rate of the shape-retentive aggregate formed on introduction into a medium and, therefore, the amount and subsequent release rate of the entrapped active agent can be further controlled. In addition, these water soluble excipients can be used to alter the porosity over time of the wound dressing formed in situ, as they dissolve away from the aggregate upon exposure to wound exudates or blood. Using one or more of the above procedures, zero-order, or at least pseudo-zero order, release rates should be attainable for a wide range of biologically active agents.

The type and amount of an agent that can be occluded by a gel particle or entrapped in a shape-retentive aggregate dressing or biomaterial of this invention depends upon a variety of factors. First and foremost, the agent cannot interfere, due to its size, surface charges, polarity, steric interactions, etc., with the formation of discrete gel particles or the coalescence of the gel particles into a shape-retentive aggregate after introduction into a medium, such as a wound, either of which would defeat the purpose of this invention. Once it is determined that the foregoing is not a problem, the size of the hydrogel particles most directly affects the quantity of substance that can be incorporated within the particle. The size of the particles themselves will dictate the maximum amount of agent that can be occluded while the polydispersity of the particles will affect the resulting pore size of aggregate dressings formed in situ. Relatively small agents, such as individual antibiotic molecules, antimicrobial agents and analgesics may be occluded in small gel nanoparticles and easily entrapped in aggregates formed from small these gel particles, while substantially larger agents such as monoclonal antibodies, proteins, peptides, polysaccharides and other macromolecules may be difficult to occlude within these nanoparticles and will require aggregate dressings comprised of much larger particles and/or broader polydispersity to entrap them efficiently.

Using the methods herein, precise control of delivery kinetics can be achieved. That is, gel particles of differing sizes and chemical compositions can be loaded with a particular agent and the agent can be released over various timeframes. In addition, some of the substance might be occluded in the gel particles and some might be entrapped in the voids between particles of the shape-retentive wound dressing aggregate to provide even more delivery flexibility.

Using the above methods, different agents, even normally incompatible agents, can be loaded into gel particles of this invention and sequentially or simultaneously released. Sequential release will prevent incompatible agents from encountering one another. Simultaneous release permits delivery of two or more non- or minimally active bioactive agents that, when combined, form a potent drug. In this manner, the formation of the active species can be postponed until the aggregate containing the precursors has been formed at the wound site when the nanoparticles combine with blood or exudate and coalesce to provide prolonged active release to the underlying wound bed.

In another aspect of this invention, gel particles of two or more different sizes and narrow polydispersity with regard to each other are used at a to form shape-retentive wound dressing aggregates of this invention. The trapping efficiency of substances and their subsequent release rate should be substantially different than those of aggregates formed using single size narrow polydispersity particles. Without being held to any particular theory, it is believed that this may be due to the possibility that, during aggregation in the presence of a substance to be entrapped, the voids between the particles comprising the wound dressing aggregate are more efficiently filled by mixed polydispersity particles. The examples which follow demonstrate that, for a specific agent of a given size, the size and ratio of sizes of particles comprising an aggregate dramatically affect a forming aggregate's efficiency in trapping an agent and its subsequent release rate. Using this approach, the release rate of a particular substance might be tailored to approach pseudo-zero order kinetics using appropriate particle sizes and ratio of sizes.

Thus, the present invention provides an extremely versatile substance delivery platform for wound dressings formed in situ, in particular with regard to biologically active agent delivery and most particularly with regard to pharmaceutical agent delivery. In a particular embodiment, wound dressings for decubitus ulcers, vascular ulcers, second, third and fourth degree burns and skin donor site with or without incorporated antibiotics, pain killers, growth factors or vascular signaling agents could be formed directly at a wound site in situ by introducing the nanoparticulate powder into or onto a wet wound and a skin donor site. A pharmaceutical agent or combination of agents may be delivered continuously over an extended time period, in bursts at specific time intervals, simultaneously after a predetermined delay time so that two or more agents can interact synergistically only after formation of the aggregate dressing containing them at a desired target site, or sequentially so that one agent can act at a target site before the next agent is released or so that two or more agents can synergistically interact.

Another embodiment of this invention is the use of the shape-retentive aggregate materials formed in situ by introducing powdered nanoparticles to bodily fluid, as biomaterials useful in orthopedic applications such as tissue scaffolding. The macroporous structure of the shape-retentive and shape-conforming aggregates of this invention provides a composition that should permit substantial ingrowth, a property not found in typical microporous bulk hydrogels. In addition, the aggregates of this invention exhibit physical properties, such as elastic, shear and bulk moduli, that are significantly improved over those of conventional bulk hydrogels. Possible orthopedic applications of the methods of this invention include, without limitation, cartilage and bone repair, meniscus repair/replacement, artificial spinal discs, artificial tendons and ligaments, and bone defect filler.

The shape retentive property of the aggregate materials of this invention and their ability to be formed in situ and retain water suggest numerous other in vivo uses. For example, a medicated or unmedicated aggregate could be molded into a soft contact lens. A soft, pliable, biocompatible drug delivery device to treat serious eye diseases could be formed in situ placing the powdered hydrogel nanoparticles in which an ocular pharmaceutical agent has been occluded or entrapped behind the eye. A shape-retentive aggregate could be formed in a periodontal pocket by introducing the nanoparticulate powder in which a bone growth factor is either occluded by the particles or entrapped in the forming aggregate. The aggregate might also have within it occluded or entrapped antibiotic for control of infection by sustained delivery of the antibiotic while bone regeneration is being stimulated through the controlled release of the bone growth factor. As an added benefit, the soft, biocompatible shape-retentive aggregate would provide comfort at the site due to its inherent softness and conformability.

The aggregates of this invention produced by the methods hereof might be used as carriers for a host of materials other than biomedical agents. For example, without limitation, metals or metal ions could be occluded in the gel particles, entrapped by the aggregate or both. The metals and/or ions would confer varying degrees of conductivity and radiopacity of the aggregates that could have other uses such as in the electrical stimulation of wound healing.

These and may other uses for the shape-retentive, shape-conforming aggregate wound dressings and biomaterials of this invention will become apparent to those skilled in the art based on the disclosures herein. Such uses are within the scope of this invention.

EXAMPLE 1

Hydrogel Nanoparticle Synthesis Using HEMA

A 500 mL media bottle equipped with a stir bar was charged with 4.52 g (34.8 mmol) hydroxyethyl methacrylate (HEMA) monomer, 77.74 mg (0.428 mmol) ethylene glycol dimethacrylate (EGDM), 0.2123 g (0.634 mmol) sodium dodecyl sulfate (SDS) and 240 mL milli-Q $H_2O$. The bottle was closed with a sparging cap and purged with $N_2$ for 1 hr at room temperature while stirring. Then, 0.166 g potassium persulfate ($K_2S_2O_8$) was dissolved into 21 mL of milli-Q $H_2O$ and added to the media bottle while stirring. The bottle was transferred to a 40° C. water bath and held there for 12 hours. The resulting suspension of hydrogel particles had an opalescent blue color. The particles were analyzed by dynamic light scattering and found to have an average radius of 36.5 nm as shown in FIG. 1. The particles were purified by tangential flow filtration and are stored in an aqueous suspension. No flocculation was observed over several months.

EXAMPLE 2

Hydrogel Nanoparticle Synthesis Using HPMA

A 150 mL media bottle equipped with a stir bar was charged with 2.532 g (17.5 mmol) of hydroxypropyl methacrylate (HPMA) monomer, 52.73 mg (0.266 mmol) of ethylene glycol dimethacrylate(EGDM) crosslinker, 107.6 mg (0.3730 mmol) sodium-dodecylsulfate (SDS), and 118 mL of nitrogen degassed Milli-Q $H_2O$. The bottle was closed and stirred to form a clear solution. In a separate vial, 83 mg of $K_2S_2O_8$ was dissolved into 2 mL of Milli-Q $H_2O$ and added to the media bottle while stirring. The media bottle with clear solution was transferred into a 40° C. water bath and held at constant temperature for 12 hours. The resulting suspension of hydrogel nanoparticles had an opalescent blue color. The particles were analyzed by laser light scattering and found to have an average particle size of 21.3 nm and a size range from 14 nm to 41 nm. The suspension had approximately 1% solid polymer by mass. To date, the suspension of hydrogel nanoparticles resisted flocculation or aggregation for two years at room temperature.

EXAMPLE 3

Hydrogel Nanoparticle Copolymer Synthesis Using HEMA and HPMA

Using the synthetic method of Example 1, copolymer nanoparticles were produced using HEMA monomer and HPMA monomer. Table 1 shows the relative masses and mmol of monomers added to the 150 mL media bottles:

TABLE 1

| Sample | Mass HEMA | mmol HEMA | Mass HPMA | mmol HPMA |
|---|---|---|---|---|
| 95:5 pHEMA:HPMA | 4.30 g | 33.06 | 0.251 g | 1.74 |
| 90:10 pHEMA:HPMA | 4.07 g | 31.32 | 0.501 g | 3.48 |
| 85:15 pHEMA:HPMA | 3.85 g | 29.58 | 0.752 g | 5.22 |
| 75:25 pHEMA:HPMA | 3.40 g | 26.10 | 1.25 g | 8.70 |
| 50:50 pHEMA:HPMA | 2.26 g | 17.40 | 2.51 g | 17.40 |

Each media bottle was then charged with 52.73 mg (0.266 mmol) EGDM, 107.6 mg (0.3730 mmol) sodium dodecylsulfate (SDS), and 118 mL of nitrogen degassed Milli-Q $H_2O$. The bottles were capped and stirred for 30 minutes at room temperature. In 5 separate vials, 83 mg of $K_2S_2O_8$ was dissolved into 2 mL of Milli-Q $H_2O$ respectively and added to each media bottle while stirring. The media bottles with clear solutions were transferred into a 40° C. water bath and held at constant temperature for 12 hours. The resulting suspension of hydrogel nanoparticles had an opalescent blue color.

EXAMPLE 4

Hydrogel Nanoparticle Synthesis Using GMA

A 2000 mL media bottle equipped with a stir bar was charged with 44.5 g (277 mmol) of glycerol methacrylate (GMA) monomer, 92 mg (0.464 mmol) of ethylene glycol dimethacrylate(EGDM) crosslinker, 2.04 g (0.3730 mmol) sodium dodecylsulfate (SDS), and 118 mL of nitrogen degassed Milli-Q $H_2O$. The bottle was closed and stirred to form a clear solution. In a separate vial, 83 mg of $K_2S_2O_8$ was dissolved into 2 mL of Milli-Q $H_2O$ and added to the media bottle while stirring. The media bottle with clear solution was transferred into a 40° C. water bath and held at constant temperature for 12 hours. The resulting suspension of hydrogel nanoparticles had an opalescent blue color. The particles were analyzed by laser light scattering and found to have an average particle size of 21.3 nm and a size range from 14 nm to 41 nm. The suspension had approximately 1% solid polymer by mass. To date, the suspension of hydrogel nanoparticles resisted flocculation or aggregation for two years at room temperature.

EXAMPLE 5

Hydrogel Nanoparticle Copolymer Synthesis Using HEMA and GMA

Using the synthetic methods as above, nanoparticles were produced using HEMA and glycerol methacrylate monomers. Table 2 shows the relative masses and mmol of monomers added to the 2000 mL media bottles.

TABLE 2

| Sample | Mass HEMA | mmol HEMA | Mass GMA | mmol GMA |
|---|---|---|---|---|
| 90:10 pHEMA:GMA | 40.0 g | 307.36 | 4.47 g | 27.78 |
| 75:25 pHEMA:GMA | 33.35 | 256.30 | 11.11 g | 69.46 |

Each media bottle was then charged with 80 mg (0.404 mmol) of EGDM crosslinker, 20.4 g (7.09 mmol) sodium dodecylsulfate (SDS), and 2000 mL of nitrogen-degassed Milli-Q $H_2O$. The bottles were closed and stirred to form clear solutions. In two separate vials, 1.44 g (6.31 mmol) of $(NH_4)_2S_2O_8$ was dissolved into 20 mL of Milli-Q $H_2O$ and added to the 2000 mL media bottles while stirring. The media bottles with clear solution were transferred into a 50° C. water bath and held at constant temperature for 12 hours. The resulting suspensions of hydrogel nanoparticles were opalescent blue in color. The particles were analyzed by laser light scattering and Table 4 shows the average particle sizes and size ranges.

EXAMPLE 6

Lyophilization of Nanoparticle Suspensions

The nanoparticle suspensions of examples 1-5 were frozen at −80° C. The solid suspensions were dried under vacuum at room temperature in a VIRTIS lyophilization system to produce a white powder. The powder was milled or sieved to produce particles of uniform sizes. The density of the milled powder was approximately 200 mg/mL and the density of the sieved particles was approximately 120 mg/mL. The particles remained as a stable powder with no change in appearance or bulk density for 6 months at room temperature.

EXAMPLE 7

Redispersion of Dry Nanoparticle Powder

The lyophilized powders of example 6 were exposed to various solvents to determine whether the powders from milling or sieving could be redispersed as suspensions. The following solvents showed the ability to redisperse the particles:

Water, ethanol, methanol, isopropanol, and butanol. Non-polar solvents such as hexane or ethyl acetate would not allow the powder to redisperse and formed insoluble masses of wetted powder when combined with the lyophilized powder.

EXAMPLE 8

Aggregation of Poly-HEMA Nanoparticle Powder in PBS

Poly-2-hydroxyethyl methacrylate lyophilized powder from example 6 was added to phosphate buffered saline solution at physiological pH and ionic strength. Within several seconds, the powder coalesced forming an integral, strong aggregate film. FIG. 1 shows a photograph of the nanoparticle powder, the powder applied to phosphate buffered saline and the resulting aggregate after formation.

EXAMPLE 9

Figure 2:
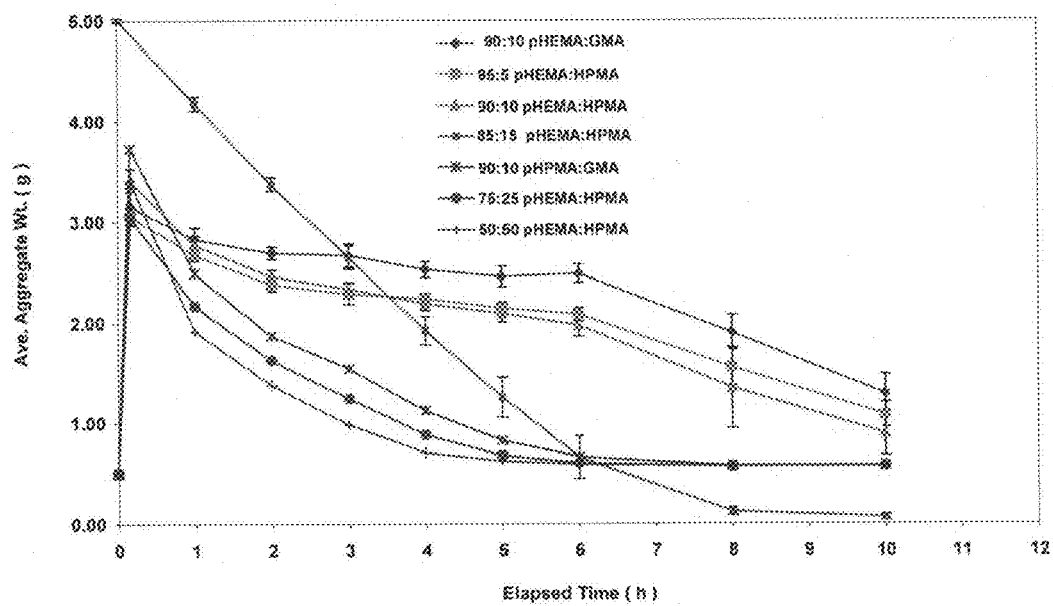
FIG. 2 is a plot showing the relative mass of an aggregate formed from 500 mg of nanoparticle powder applied to phosphate buffered saline and changes in the mass of those aggregates over time at constant temperature and humidity. The aggregates had different chemical compositions.

Rate of Water Loss after Hydration and Aggregation of Copolymer Nanoparticle Powders in PBS Several nanoparticle powders of different chemical compositions were exposed to phosphate buffered saline. FIG. 2 shows the results of the plots for water loss for these copolymer aggregates composed of varying ratios of HEMA monomer, glycerol methacrylate and hydroxypropyl methacrylate.

In FIG. 2, the plots show the average weight for a hydrogel nanoparticle aggregate formed using 500 mg of powder in phosphate buffered saline at pH=7.4. The aggregates were weighed and returned and allowed to dry in an environmental chamber at 37° C. The plot shows that the aggregate materials containing GMA have the highest initial water adsorption, due to its inherent higher hydrophilic character than HEMA or HPMA. However, the loss of water over time is more rapid for these aggregates. The copolymers of pHEMA:HPMA have a lower initial solution adsorption but do not lose water mass as rapidly.

EXAMPLE 10

Rheology Data for Various Aggregate Films Formed from Nanoparticle Powders and PBS Table 3 below shows relative elasticities for different types of nanoparticle aggregates. For a given study, tension was placed on a nanoparticle aggregate after formation from a powder and PBS while hydrated using a Duofield tensiometer actuating the aggregate at a rate of 1 mm/second. Aggregates were cut to a dogbone shape 1 cm in length and having a neck with dimensions of 1 mm×2 mm. Aggregates were stretched until failure and the maximum tension at failure was observed and recorded for three replicate trials.

TABLE 3

| Sample | Elongation (mm) (StDev) | Tension at Failure (g) (StDev) |
|---|---|---|
| pHEMA | 54 mm (3.54) | 0.58 g (1.21) |
| 90:10 pHEMA:GMA | 98 mm (4.32) | 0.12 g (1.13) |
| pHPMA | 6 mm (2.17) | 5.9 g (1.98) |
| 90:10 pHPMA:GMA | 69 mm (7.83) | 0.19 g (3.34) |
| 95:5 pHEMA:HPMA | 46 mm (8.21) | 0.71 g (1.31) |
| 90:10 pHEMA:HPMA | 41 mm (3.59) | 1.3 g (2.91) |
| 85:15 pHEMA:HPMA | 38 mm (3.42) | 2.7 g (1.83) |
| 75:25 pHEMA:HPMA | 22 mm (4.31) | 3.8 g (1.95) |
| 50:50 pHEMA:HPMA | 11 mm (3.11) | 5.1 g (0.61) |

General trends in the above data show that the materials containing GMA coalesce to form aggregates, which have a high elasticity but very low breaking strengths under elongation. Ratios of higher GMA (15% or more) resulted in aggregates which were very elastic but had little structural integrity; the materials stretched beyond the limits of the actuator, however sharp changes in pressure resulted in fracture and failure of the material. The addition of the comonomer HPMA to the HEMA resulted in stronger, less elastic materials, which maintained some of the elasticity of the pHEMA but increased the breaking strength as the more hydrophobic HPMA comonomer was increased. This reduction of elasticity is due to the lower amount of absorption and adsorption of PBS by the powder when the aggregate forms.

EXAMPLE 11

Figure 3:
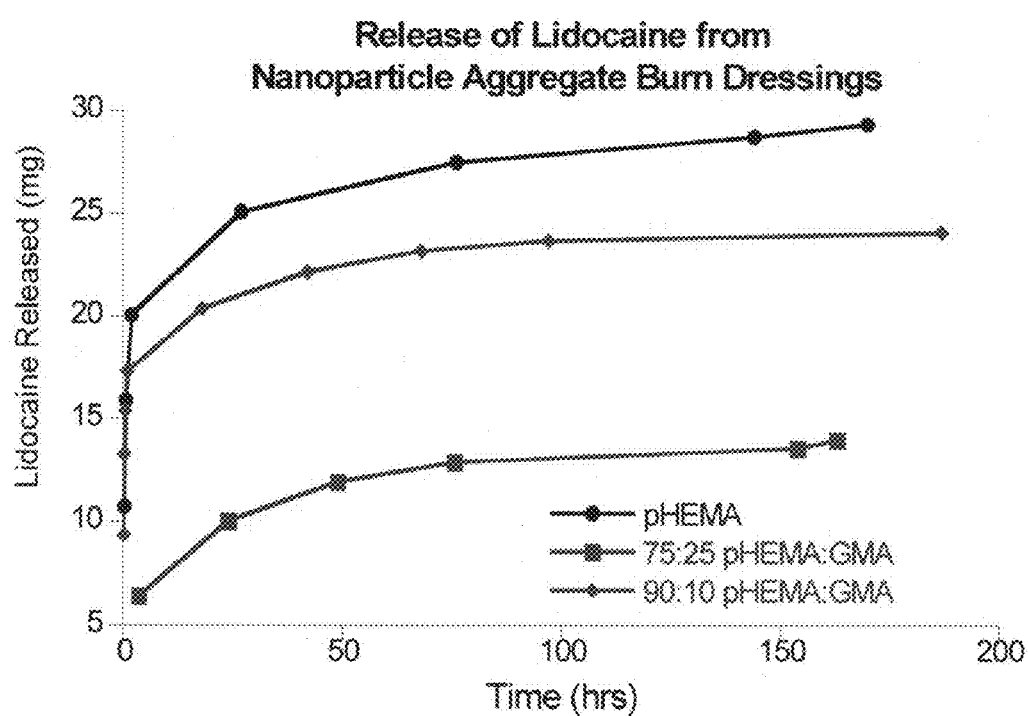
FIG. 3 is a plot showing the release of lidocaine from nanoparticle aggregate burn dressings composed of pHEMA and copolymers of HEMA and GMA.
Figure 4:
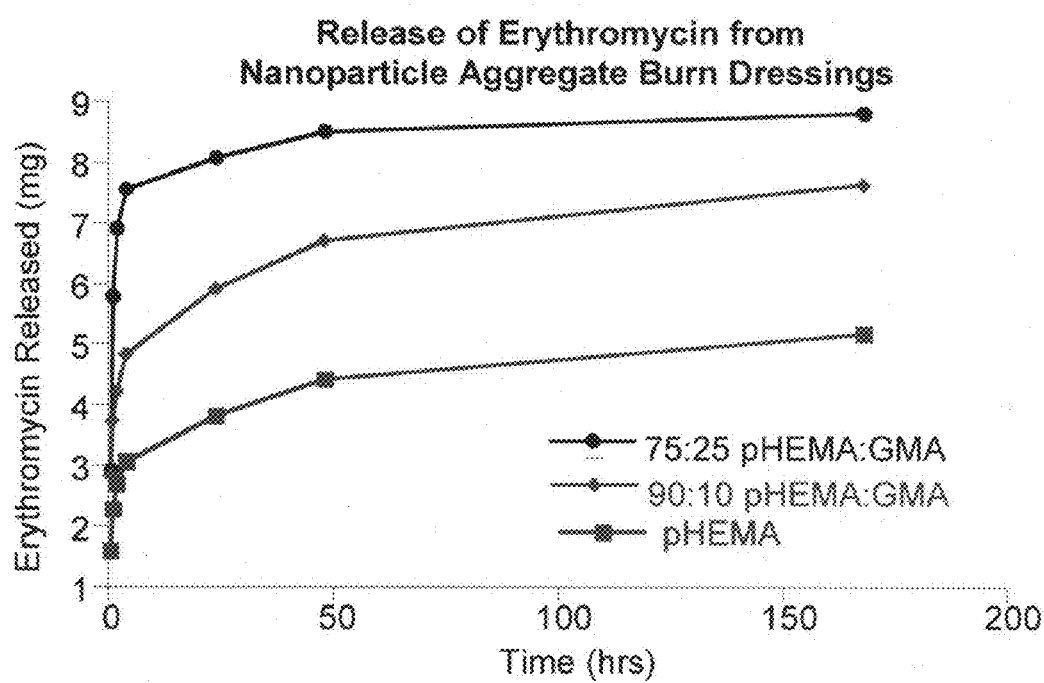
FIG. 4 is a plot showing the release of erythromycin from nanoparticle aggregate burn dressings composed of pHEMA and copolymers of HEMA and GMA.

Dry Blending of Bioactive Compounds with Nanoparticle Powder to Produce Medicated Biomaterials Poly-HEMA nanoparticle powder and HEMA/GMA copolymer nanoparticle powders were dry blended with lidocaine or erythromycin powder and upon exposure to PBS, aggregates formed trapping the active between the particles comprising the aggregate. The active is then released at a controlled rate, dependent upon the particle size, the hydrophilic/hydrophobic character of the polymer or copolymer nanoparticles comprising the aggregate and the physical properties of bioactive compound used. As shown in FIGS. 3 and 4, the release rate can be tailored to provide a specific level of active over a prolonged period of time. FIG. 3 shows the release of lidocaine from three different aggregates and FIG. 4 shows the release of erythromycin.

The FIGS. 3 and 4 show that for compositionally identical aggregates, the molecule that is trapped and subsequently released can have different release profiles. This is due to the physical properties of the molecule that is entrapped between the nanoparticles comprising an aggregate and the hydrophilic/hydrophobic character of the aggregate. For example, the relatively hydrophobic lidocaine molecule is released at a slower rate as the amount of the hydrophilic glycerol methacrylate comonomer is increased in the copolymer nanopartilce powder and the rate of erythromycin increases since it is a more hydrophilic active.

EXAMPLE 12

Incorporation of 1,10 Phenanthroline in PHEMA/PHPMA Nanoparticle Aggregates 1,10 phenanthroline, a hydrophobic protease inhibitor that coordinates to metals in metalloproteases and interferes with enzyme kinetics, was incorporated into nanoparticle aggregates composed of mixtures of HEMA and HPMA nanoparticle powders. The effective concentration of the metalloprotease is 0.1 mmol/L and it has a UV-Vis absorption spectrum with a maximum absorbance at 510 nm (McCarty, R. E. *Analytical Biochem.*, 205, 371-372, 1992). A controlled release study was performed by milling 1 mg of 1,10 phenanthroline with 100 mg of hydrogel nanoparticle powder and adding this to 100 mL of phosphate buffered saline to produce the respective aggregate. The aggregates were transferred to 100 mL of PBS and placed in a water bath at 37° C. The amount of 1,10 phenanthroline eluting into PBS was spectophotometrically determined at different time intervals. Poly-HEMA nanoparticles and pHPMA nanoparticles were each produced with the following different average diameters as shown in Table 4

TABLE 4

| Sample | Diameter |
|---|---|
| pHEMA (A) | 100 nm |
| pHEMA (B) | 42 nm |
| pHPMA (A) | 96 nm |
| pHPMA (B) | 38 nm |

The particles were combined in the ratio of 85:15 pHEMA:pHPMA weight to weight and the mixed powders were milled with 1:10 phenanthroline to form composites containing 1 milligram of 1:10 phenanthroline per 100 mg of powder.

Figure 5:
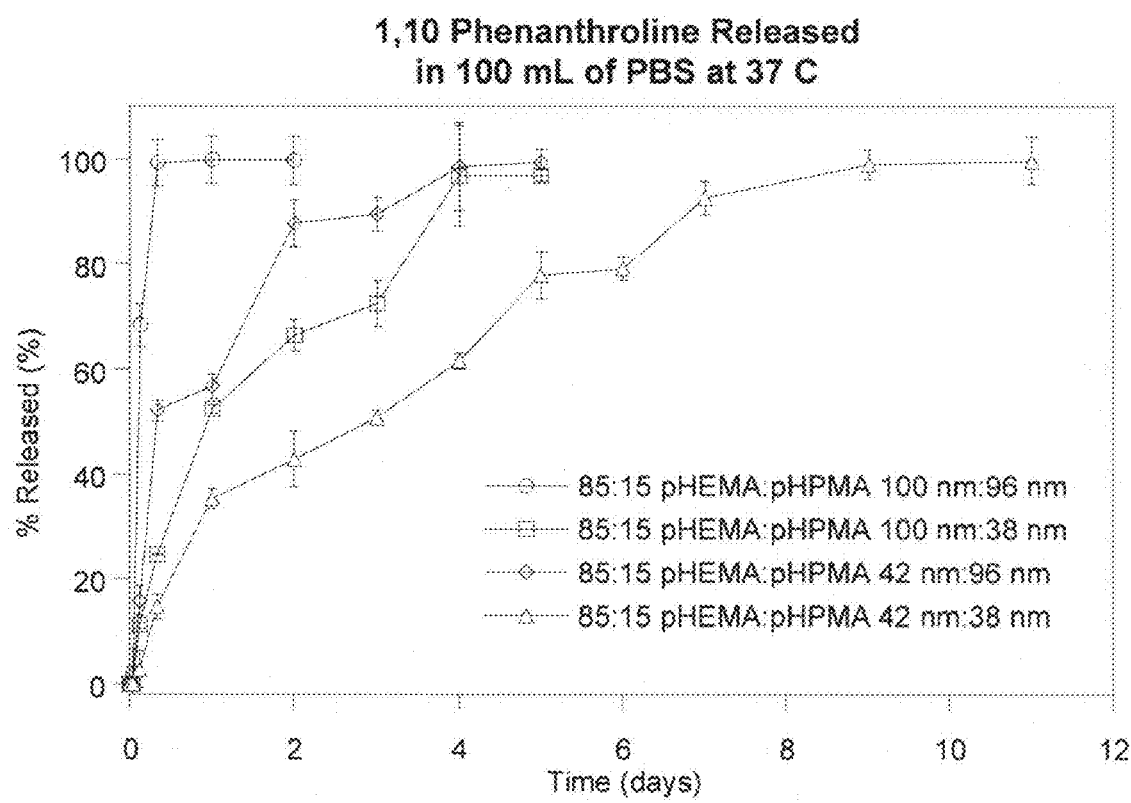
FIG. 5 is a plot showing the release of 1,10-phenanthroline from nanoparticle powders composed of mixtures of PHEMA and pHPMA particles with different diameters.
Figure 6:
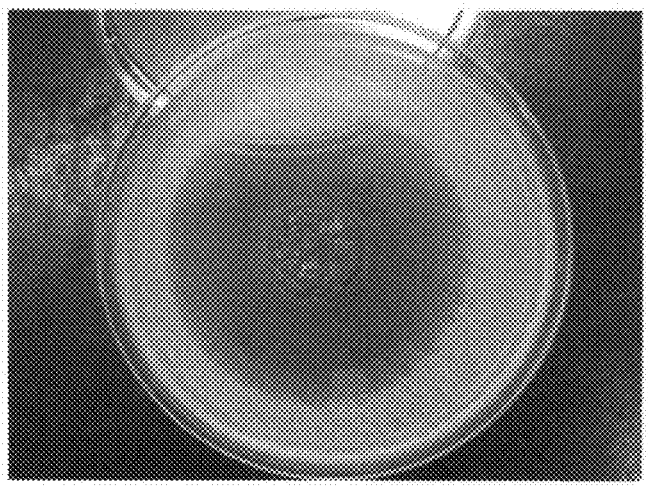
FIG. 6 shows the inhibition of *staph aureus* bacteria on a petri-dish from a nanoparticle aggregate loaded with doxycycline and rifampin.
Figure 7:
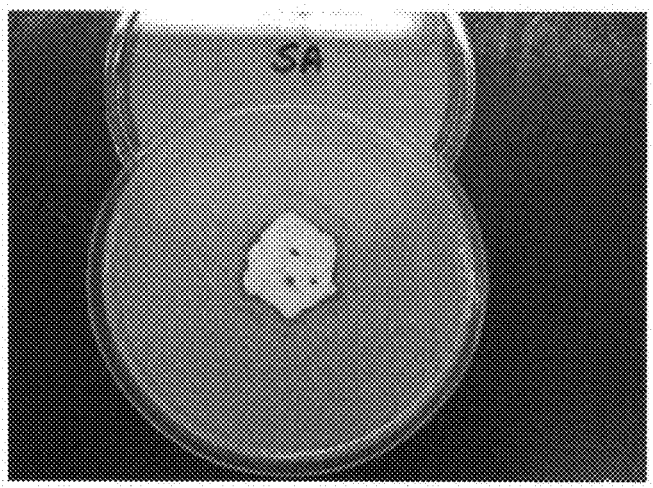
FIG. 7 shows the inhibition of *staph aureus* bacteria on a Petri-dish from a control nanoparticle aggregate without any antibiotic.

FIG. 5 shows the in vitro release of 1,10 phenanthroline from aggregate biomaterials composed of mixtures of nanoparticles. The plot demonstrates that it is possible to regulate the release of 1,10 phenanthroline from nanoparticle aggregates using different sizes and chemical compositions of nanoparticles to give controlled doses in time periods from 1 day to 13 days.

EXAMPLE 13

In Vivo Bacteria Killing Study

A study was designed to determine the effectiveness of controlled release doxycycline and rifampin from nanoparticle aggregates in cultures of infectious bacteria commonly found in burns. The initial study was designed to determine if the controlled release of the drugs was sufficient to perform effective killing of the bacteria over a 14-day period. To simulate a continuous infection, three bacterial strains, *Staph Aureus, Enterococcus*, and *Pseudomonas* were each plated out onto separate agar plates. 150 mg of nanoparticle aggregate containing 3 mg of doxycycline and 1.5 mg of rifampin were prepared by dry blending the antibiotics with nanoparticle powders and then adding the powder to 5 mL of phosphate buffered saline. The intact aggregate was allowed to form for 5 minutes. The aggregate was carefully transferred to colonies of bacteria on dishes and the zone of inhibition was photographed as shown below. Every 24 hours, a fresh colony of bacteria was incubated and the same aggregate was transferred to the new plate to determine the inhibition of the bandage with antibiotic over time. The nanoparticle aggregate with controlled released antibiotics was compared to a commercial, non-controlled release, silver impregnated antibiotic bandage.

Figure 8:
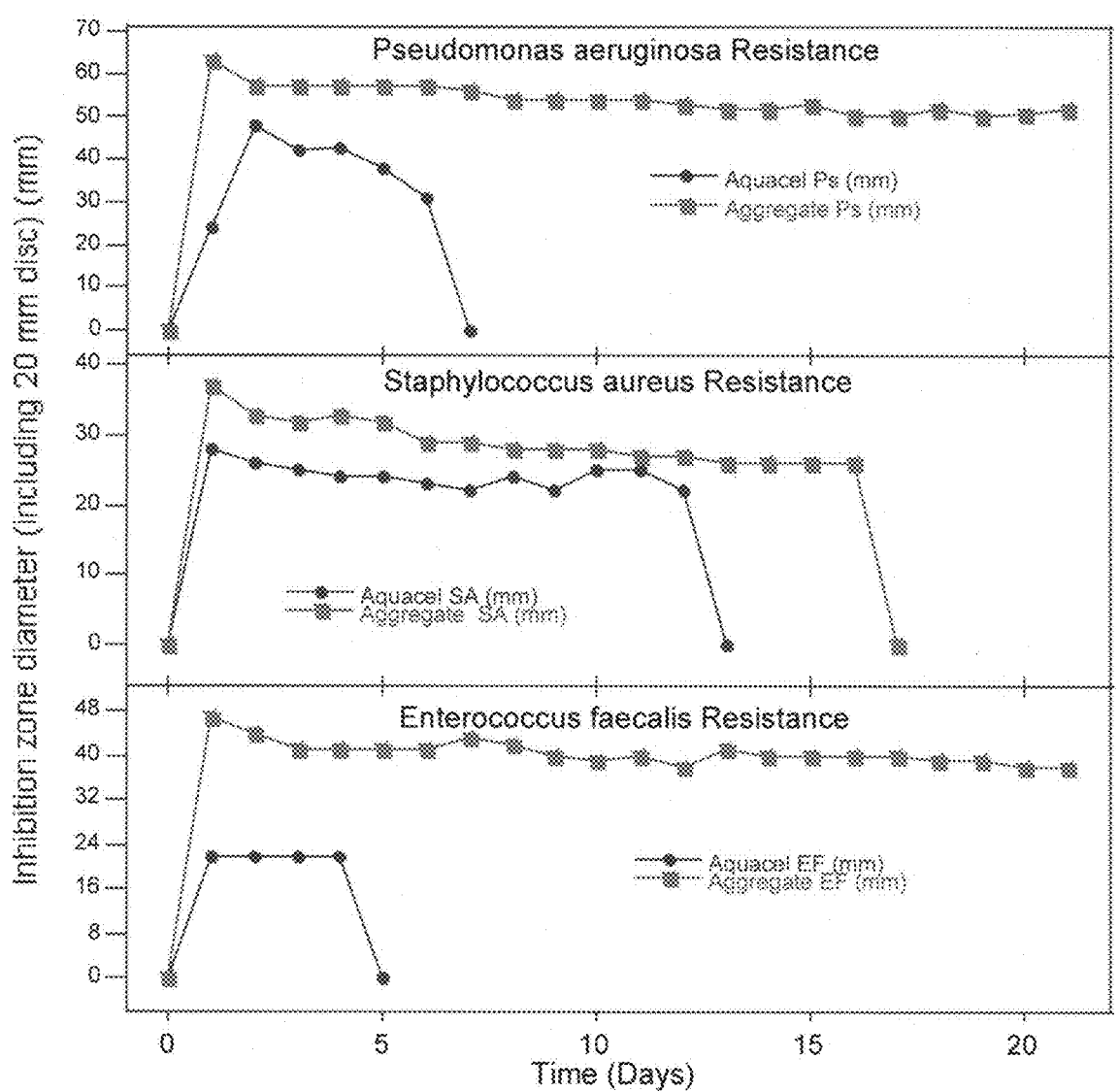
FIG. 8 shows plots of the inhibition of the bacteria strains *Pseudomonas aeruginosa, Staphylococcus aureus*, and *Enterococcus faecalis* over time with nanoparticle aggregates containing doxycycline and rifampin compared to a commercial silver antibiotic impregnated bandage.

Bacteria Tested in Project:
*Staphylococcus aureus* ATCC 25923 (referred to as SA)
*Pseudomonas aeruginosa* ATCC 27853 (referred to as Ps)
*Enterococcus faecalis* ATCC 51299 (referred to as EF)
Material Used:
BBL Prompt Inoculation System for use with disc diffusion susceptibility tests Mueller Hinton agar
Protocol: Place 20 mm punch of Aquacel Ag commercial bandage or the aggregate containing both actives on the surface of the inoculated disc. Transfer each respective dressing to newly inoculated disc every 24 hours for duration of study and observe the zone of inhibition. In this study, bacterial inhibition was measured as the zone of inhibition around the disc formed in 24 hours for a new plate with colonies incubated for 6 hours. The total inhibition for each included the 20 mm disc of either the Aquacel material or aggregate dressing. Samples tested on Mueller Hinton agar inoculated with separate strains of bacterium (BBL Prompt method used for diluting the bacteria to the appropriate $1.5 \times 10^8$ colony forming units per ml(CFU/mL). The plot of inhibition for each bacteria is shown in FIG. 8.

From the above studies, the aggregate dressing material provides inhibition of *Staphylococcus aureus, Pseudomonas aeruginosa*, and *Enterococcus faecalis* over 18-21 days. A commercial bandage of 1% silver impregnated hydrogel gauze provides inhibition for 10-12 days for the same strains of bacteria.

EXAMPLE 14

Wound Healing Studies

Figure 9:
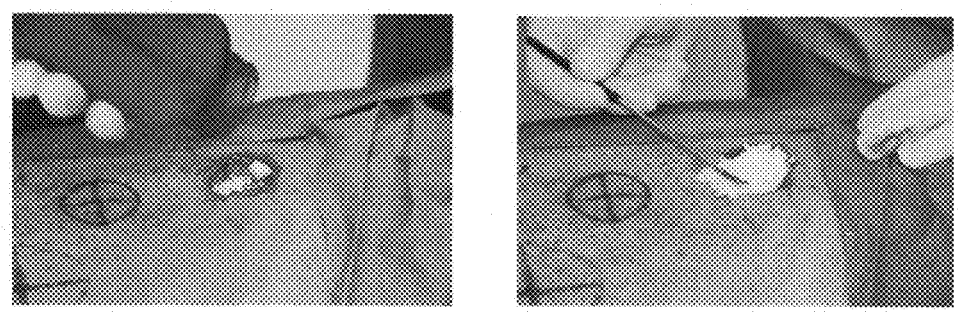
FIG. 9 shows nanoparticle powder being applied to a full thickness wound in a porcine model.

The images in FIG. 9 show the non-medicated nanoparticle powder (a mixture of 85% poly-HEMA nanoparticles and 15% poly-HPMA nanoparticles) applied to wounds of different diameters (2 cm, 4 cm and 6 cm respectively) which were partial thickness (2 cm deep) at different time points during healing. The powder is applied directly on a wound and utilizes the exudates to form an aggregate dressing.

In this study, the nanoparticle powder was applied to the exuding wound surface and pressed into place. No secondary dressing was applied. The standard of care commercial hydrogel dressing was applied to the surface of the wound and required a secondary dressing and daily changing. The nanoparticle aggregate dressing required no changing of the dressing during wound healing and showed no evidence of inflammation such as redness at the margin or elevated TNF-α levels.

Figure 10:
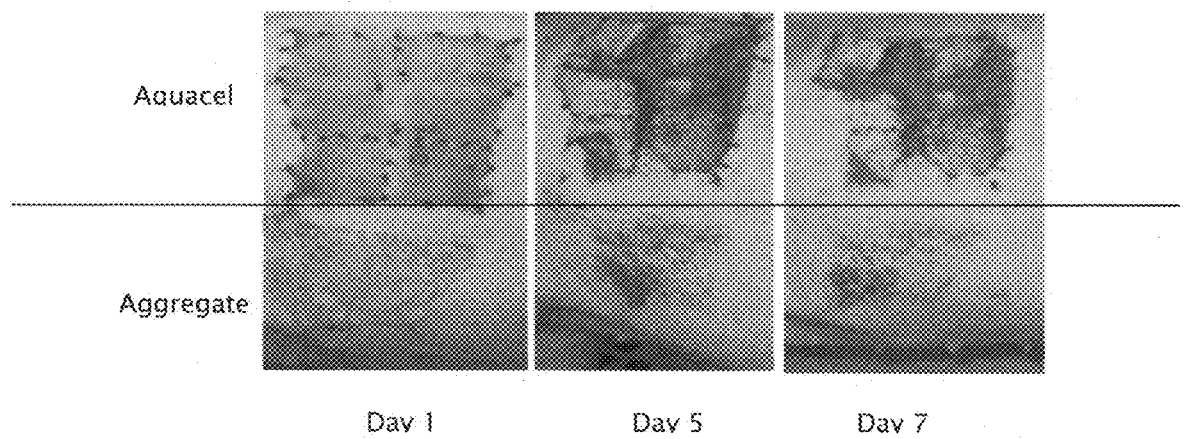
FIG. 10 shows the nanoparticle powder and a commercial hydrogel dressing applied to skin graft donor sites in a porcine model with healing over time.

The dressing has also been applied to skin graft donor sites in a porcine animal model. FIG. 10 shows the healing results over seven days after forming an aggregate dressing on a porcine skin graft donor site as compared to Aquacel.

FIG. 10 shows that the Aggregate material can be used as an effective bandage for skin graft donor sites with healing equivalent to or better than a commercial bandage.

EXAMPLE 15

Incorporation of Growth Factors with Nanoparticle Powders and Application of Growth Factor Releasing Bandages in a Wound Healing Model Hydrogel nanoparticle powders composed of 85:15 pHEMA:pHPMA nanoparticles were combined with the growth factors, vascular endothelial growth factor (VEGF) and platelet derived growth factor (PDGF) and applied to wounds. Powders were prepared as follows:

105 mL of a suspension of 85:15 pHEMA:pHPMA nanoparticles in water were combined with 5 micrograms of VEGF protein. The suspension was mixed thoroughly to insure homogeneity and lyophilized yielding 2 g of powder which was divided into 5, 400 milligram fractions. Each fraction contained 1 microgram of VEGF.

105 mL of a suspension of 85:15 pHEMA:pHPMA nanoparticles in water were combined with 20 micrograms of PDGF protein. The suspension was mixed thoroughly to insure homogeneity and lyophilized to yield 2 g of powder which was divided into 5, 400 milligram fractions. Each fraction contained 4 micrograms of PDGF protein.

105 mL of a suspension of 85:15 pHEMA:pHPMA nanoparticles in water were combined with 5 micrograms of VEGF protein and 20 micrograms of PDGF protein. The suspension was mixed thoroughly to insure homogeneity and lyophilized to yield 2 g of powder which was divided into 5, 400 milligram fractions. Each fraction contained 1 microgram of VEGF and 4 micrograms of PDGF protein.

1 inch by 1 inch full thickness wounds were formed on a pig in a grid of 4 wounds×4 wounds for a total of 16 wounds. Each wound was covered with one of the four types of bandages:

Nanoparticle powder containing 1 microgram of VEGF per 400 milligrams of bandage.

Nanoparticle powder containing 4 micrograms of PDGF per 400 milligrams of bandage.

Nanoparticle powder containing both 1 microgram of VEGF and 4 micrograms of PDGF per 400 mg of bandage.

Control nanoparticle powder without growth factors.

The wounds were not covered with secondary bandages. Biopsies were taken at 2, 7, 14 and 21 days from each wound site and the samples were studied for histology.

Figure 11:
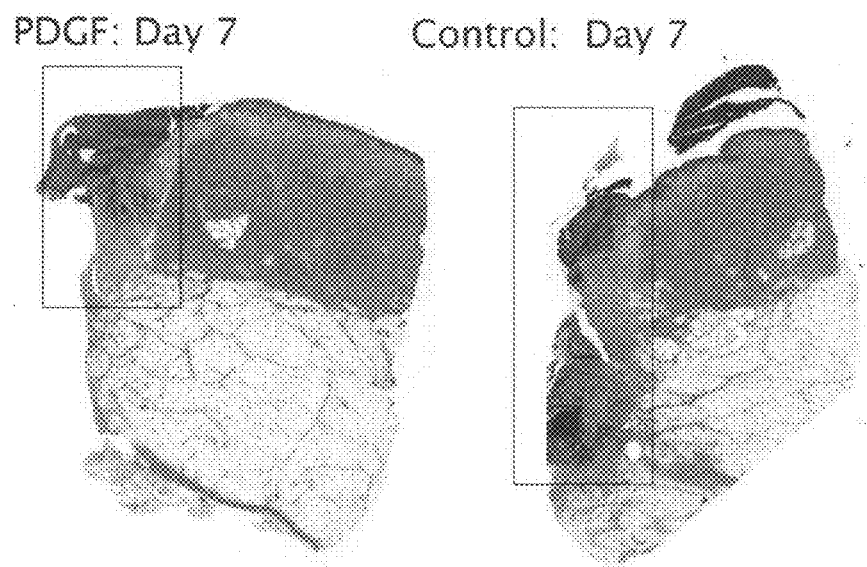
FIG. 11 shows the histology for wounds treated with nanoparticle aggregate containing platelet derived growth factor and a control aggregate containing no growth factor.

Histology of Control and PDGF-Treated Wound is shown in FIG. 11. In the histology images shown, the biopsy on the right was from a wound treated with the control bandage containing no active growth factor. The biopsy on the left was from a wound treated with PDGF-loaded nanoparticle aggregate bandage Both biopsies are at day 7. In the control, the wound bed is much deeper at 7 days and shows much less granulation. In addition, there was greater fibroblast recruitment in the PDGF loaded wound. The wound area is shown with the box in each histology image while the right side of each image shows healthy tissue removed at the wound margin in the biopsy. Similar results were found on day 14 and 21, with a significant increase in granulation.

Figure 12:
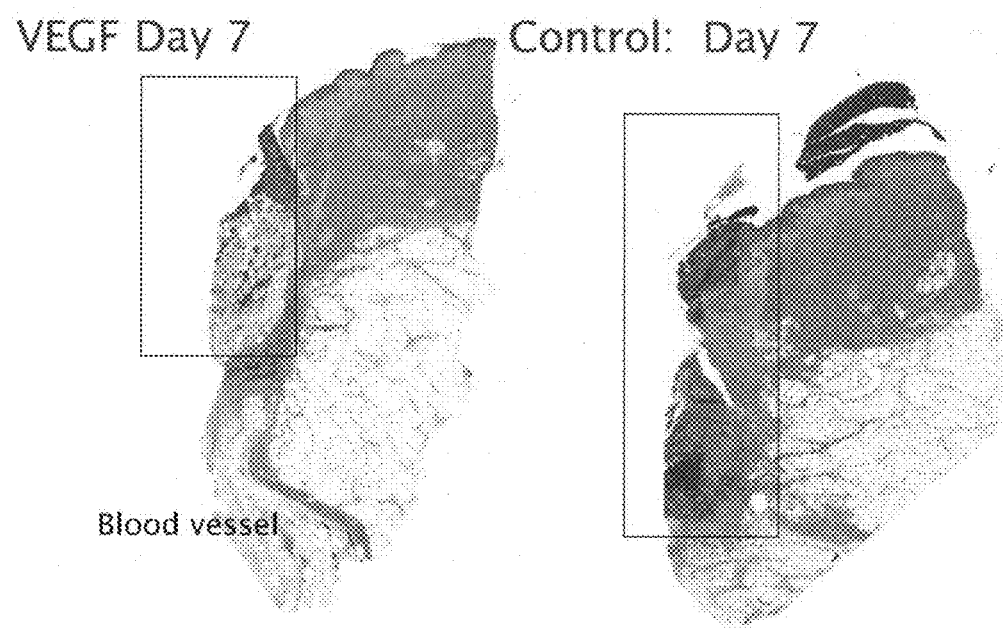
FIG. 12 shows the histology for wounds treated with nanoparticle aggregate containing vascular endothelial growth factor and a control aggregate containing no growth factor.

Histology of Control and VEGF-Treated Wound is shown in FIG. 12. In the histology images shown, the biopsy on the right was from a wound treated with the control bandage containing no active growth factor. The biopsy on the left was from a wound treated with VEGF-loaded nanoparticle aggregate bandage. The bandage contained 1 microgram of VEGF per gram of dressing. Both biopsies are at day 7.

In the control the wound is much deeper at 7 days and shows much less granulation. In contrast, the VEGF treated wound shows a dramatic increase in vasculature within the wound bed. The wound area is shown with the box in each histology image while the right side of each image shows healthy tissue removed at the wound margin in the biopsy.

Figure 13:
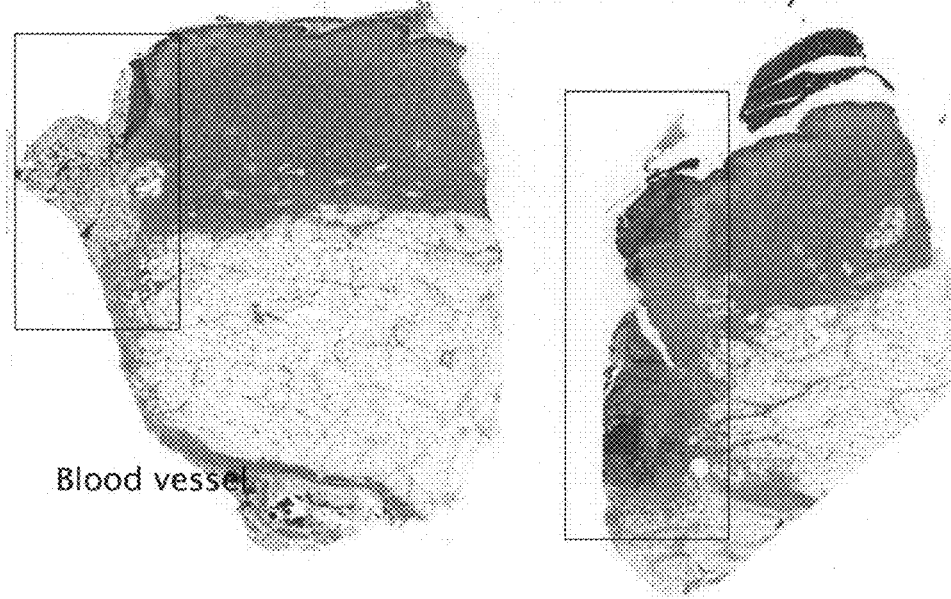
FIG. 13 shows the histology for wounds treated with nanoparticle aggregate containing a combination of platelet derived growth factor and vascular endothelial growth factor and a control aggregate containing no growth factor.

Histology of control and combined VEGF and PDGF-treated wound is shown in FIG. 13. In the histology images shown, the biopsy on the right was from a wound treated with the control bandage containing no active growth factor. The biopsy on the left was from a wound treated with combined PDGF and VEGF-loaded nanoparticle aggregate bandage. Both biopsies are at day 7.

In the control the wound is much deeper at 7 days and shows much less granulation. In addition, there is a drastic increase in vasculature within the wound bed and an increased rhett formation in the wound margin. The wound area is shown with the box in each histology image while the right side of each image shows healthy tissue removed at the wound margin in the biopsy. It is clear from the above experiments that the incorporation of a growth factor or combination thereof in the nanoparticle powder can have a significant affect in wound healing.

EXAMPLE 16

Producing a Nanoparticle Aggregate Dressing In Situ on a Non-Exuding Skin Surface A flowable gel formulation comprising nanoparticle powder, ethanol and polyethylene glycol-400 was produced as follows:

An amount of PHEMA nanoparticle suspension as prepared according to example 1 is mixed with an amount of PHPMA nanoparticle suspension prepared according to Example 2 such that the combined suspension represents 85% pHEMA and 15% pHPMA. The combined suspension is lyophilized, and the resulting powder is brushed through a 150 micron sieve and bagged for storage.

1.15 g of the sieved nanoparticle powder is placed in a 100 ml beaker and a mixture of 1 g of PEG400, 3 g of ethanol and 0.10 g of deionized water is poured into the beaker containing the powder. This powder is mixed thoroughly with the liquid and initially forms a paste. The paste transitions into a viscous gel within 30 seconds. The gel is placed into heat sealable dispensing tubes for storage.

Upon application to intact skin, the alcohol evaporates leaving behind a plasticized, dressing aggregate that conforms to every irregular surface and adheres intimately to the underlying skin.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed:

1. A dry powder of polymeric nanoparticles that will form a shape-retentive aggregate upon exposure to a physiological medium or other medium of similar ionic strength, prepared by a method comprising:
   (a) polymerizing an effective amount of a monomer or two or more monomers, selected from the group consisting of a 2-alkenoic acid, a hydroxy (2C-4C) alkyl 2-alkenoate, a dihydroxy (2C-4C) alkyl 2-alkenoate, a hydroxy (2C-4C) alkoxy (2C-4C) alkyl 2-alkenoate, a (1C-4C) alkoxy (2C-4C) alkoxy (2C-4C) alkyl 2-alkenoate and a vicinyl epoxy (1C-4C) alkyl 2-alkenoate, a polar liquid or a mixture of two or more miscible liquids, at least one of which is polar, and from about 0.01 to about 0.1 weight percent of surfactant to produce a suspension of a plurality of polymeric nanoparticles wherein the polymeric nanoparticles have an average diameter of from about 20 to about 300 nm; and
   (b) removing the liquid(s) from the suspension in such a manner as to prevent aggregation and such that the amount of liquid(s) remaining in the dry powder is less than 10% by weight wherein the percentage is based on the total weight of the dry powder.

2. The dry powder of claim 1, wherein the polymeric nanoparticles are about the same average diameter, are formed from one or more monomers and are of a narrow polydispersity.

3. The dry powder of claim 1, wherein the polymeric nanoparticles are of differing average diameter, are formed from one or more monomers and are of a narrow polydispersity.

4. The dry powder of claim 1, wherein the polymeric nanoparticles are formed from one or more monomers and are of a broad polydispersity.

5. The dry powder of claim 1, wherein the step a) further comprises:
   adding one or more first working substance(s) in an amount effective to give a first working substance-containing liquid, wherein after polymerization, a portion of the first working substance-containing liquid is occluded by the polymeric nanoparticles;

and step b) further comprises:
adding one or more second working substance(s) in an effective amount to the dry polymeric nanoparticles and dry blending to give a second working substance-containing particulate powder, wherein the first working substance(s) may be the same as or different than the second working substance(s).

6. The dry powder of claim 1, wherein the monomer(s) are selected from the group consisting of acrylic acid, methacrylic acid, 2-hydroxyethyl acrylate, 2-hydroxyethylmethacrylate, diethyleneglycol monoacrylate, diethyleneglycol monomethacrylate, 2-hydroxypropyl acrylate, 2-hydroxypropyl methyacrylate, 3-hydroxypropyl acrylate, 3-hydroxypropyl methacrylate, dipropylene glycol monoacrylate, dipropylene glycol monomethacrylate, 2,3-dihydroxypropyl methacrylate, glycidyl acrylate, glycidyl methacrylate and a combination of two or more thereof.

7. The dry powder of claim 6, wherein the monomer(s) are selected from the group comprising methacrylic acid, 2-hydroxyethyl methacrylate, 2-hydroxypropyl methacrylate, 3-hydroxypropyl methacrylate, glycerol methacrylate and a combination of two or more thereof.

8. The dry powder of claim 7, wherein the liquid(s) are selected from the group consisting of water, a (1C-10C) alcohol, a (2C-8C)polyol, a (1C-4C)alkyl ether of a (2C-8C) polyol, a (1C-4C)acid ester of a (2C-8C)polyol, a hydroxy-terminated polyethylene oxide, a polyalkylene glycol and a hydroxy(2C-4C)alkyl ester of a mono, di- or tricarboxylic acid.

9. The dry powder of claim 8, wherein the liquid(s) are selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hydroxyethyl)citrate, di(hydroxypropyl)oxalate, glyceryl diacetate, and glyceryl monobutyrate.

10. The dry powder of claim 9, wherein the liquid is water.

11. The dry powder of claim 1, wherein the step a) further comprises adding from about 0.1 to about 15% mol percent of a cross-linking agent.

12. The dry powder of claim 11, wherein the cross-linking agent is selected from the group consisting of ethylene glycol diacrylate, ethylene glycol dimethacrylate, 1,4-dihydroxybutane dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, diallyl tartrate, diallyl malate, divinyl tartrate, triallyl melamine, N,N'-methylene bisacrylamide, diallyl maleate, divinyl ether, 1,3-diallyl 2-(2-hydroxyethyl) citrate, vinyl allyl citrate, allyl vinyl maleate, diallyl itaconate, di(2-hydroxyethyl) itaconate, divinyl sulfone, hexahydro-1,3,5-triallyltriazine, triallyl phosphite, diallyl benzenephosphonate, triallyl aconitate, divinyl citraconate, trirnethyloipropane trimethacrylate and diallyl fumarate.

13. The dry powder of claim 12, wherein the cross-linked polymeric strands of the nanoparticles have an average molecular weight of from about 3,000 to about 2,000,000.

14. The dry powder of claim 1, wherein the step a) further comprises adding an effective amount of one or more working substance(s) to the polar liquid(s) prior to polymerization providing working substance-containing polymeric nanoparticles.

15. The dry powder of claim 14, wherein the effective amount of the working substance-containing polymeric nanoparticles occlude from about 0.1 to about 90 weight percent working substance(s)-containing liquid.

16. The dry powder of claim 1, wherein the step a) further comprises:
adding one or more first working substance(s) in an amount effective to give a first working substance-containing liquid, wherein after polymerization, a portion of the first working substance-containing liquid is occluded by the polymeric nanoparticles;
and step b) further comprises:
adding one or more second working substance(s) in an effective amount to the dry polymeric nanoparticles and dry blending to give a second working substance-containing particulate powder, wherein the first working substance(s) may be the same as or different than the second working substance(s).

17. The dry powder of claim 16, wherein:
from 0.1 to 90 weight percent of the first working substance(s) is occluded by the plurality of polymeric nanoparticles; and
from 0.1 to 90 weight percent of the second working substance(s) is entrapped between the nanoparticles.

18. The dry powder of claim 1 wherein the step b) further comprises:
adding one or more working substance(s) to the dry powder and blending to provide a working substance(s)/particulate powder composite.

19. The dry powder of claim 18, wherein the working substance(s)/particulate powder composite contains from about 1 to 90 weight per cent of working substance(s).

20. The dry powder of claim 15, wherein the working substance(s) comprise one or more biomedical agent(s), which may be the same or different.

21. The dry powder of claim 20, wherein the biomedical agent(s) comprises/comprise one or more tissue scaffold materials or growth factors.

22. The dry powder of claim 20, wherein one or more of the biomedical agent(s) comprise(s) cells or platelets.

23. The dry powder of claim 20, wherein one or more of the biomedical agent(s) comprise(s) one or more pharmaceutical agent(s).

24. The dry powder of claim 23, wherein the pharmaceutical agent(s) further comprises/comprise one or more pharmaceutically acceptable excipient(s).

25. The dry powder of claim 23, wherein the pharmaceutical agent(s) comprise(s) a peptide, a protein or a polysaccharide.

26. The dry powder of claim 25, wherein the pharmaceutical agent(s) is/are useful for the treatment of wounds.

27. The dry powder of claim 23, wherein the pharmaceutical agent(s) is/are useful for the treatment of cancer.

28. The dry powder of claim 23, wherein the pharmaceutical agent(s) is/are useful for the treatment of pain.

29. The dry powder of claim 23, wherein the pharmaceutical agent(s) is/are useful for the treatment of infection.

30. The dry powder of claim 23, wherein the pharmaceutical agent(s) is/are useful for the treatment of diseases of the eye.

31. The dry powder of claim 23, wherein the pharmaceutical agent(s) is/are growth factors.

32. The dry powder of claim 1, further comprising one or more pharmaceutically acceptable excipients.

33. The dry powder of claim 32, wherein one or more pharmaceutically acceptable excipients is from about 1 to about 50 weight per cent of the dry powder.

34. The dry powder of claim 32, wherein the pharmaceutically acceptable excipient(s) is/are a water soluble filler material(s).

35. A method of forming a shape-conforming, shape-retentive aggregate dressing in situ on a wet wound site, comprising applying the dry powder of claim 1 to the wet wound site.

36. A method of forming a shape-conforming, shape-retentive aggregate biomaterial in vivo in or on a wet bodily tissue, comprising applying the dry powder of claim 1 on the wet bodily tissue.

37. A method of treatment of a wound, comprising applying an effective amount of the dry powder of claim 1.

38. The method of claim 37, wherein the dry powder further comprises an effective amount of one or more tissue scaffold materials or growth factors.

39. The method of claim 38, wherein the dry powder further comprises an effective amount of collagen.

40. The method of claim 38, wherein the dry powder further comprises an effective amount of hyaluronic acid.

41. The method of claim 37, wherein the dry powder further comprises an effective amount of pharmaceutical agent(s).

42. The method of claim 41, wherein the pharmaceutical agent(s) are selected from the group consisting of the pharmaceutical agent(s) useful for the treatment of wounds, for the treatment of cancer, for the treatment of pain, for the treatment of ocular disease, the pharmaceutical agent(s) that are growth factors and antibiotics.

43. The method of claim 42, wherein the pharmaceutical agent is lidocaine.

44. The method of claim 42, wherein the pharmaceutical agent is erythromycin.

45. The method of claim 42, wherein the pharmaceutical agents are doxycycline and rifampin.

46. The method of claim 42, wherein the pharmaceutical agents comprise VEGF polypeptide(s) and/or PDGF polypeptide(s).

47. The dry powder method of claim 1, wherein the liquid is removed by a process comprising spray-drying or lyophilization.

48. The dry powder of claim 1, wherein the powder forms a shape retentive aggregate upon application on or in a wet wound.

\* \* \* \* \*